United States Patent
Devraj et al.

(10) Patent No.: US 9,765,093 B2
(45) Date of Patent: Sep. 19, 2017

(54) AZA-BENZIMIDAZOLE INHIBITORS OF PAD4

(71) Applicant: Padlock Therapeutics, Inc., Princeton, NJ (US)

(72) Inventors: Rajesh Devraj, Chesterfield, MO (US); Gnanasambandam Kumaravel, Lexington, MA (US); Laura Gleave, Abingdon (GB); Adrian Kotey, Abingdon (GB); Thomas Krulle, Abingdon (GB); Cristina Lecci, Abingdon (GB); Heather Tye, Abingdon (GB); Ian Wigginton, Abingdon (GB)

(73) Assignee: Padlock Therapeutics, Inc., Princeton, NJ (US)

( * ) Notice: Subject to any disclaimer, the term of this patent is extended or adjusted under 35 U.S.C. 154(b) by 0 days.

(21) Appl. No.: 15/374,208

(22) Filed: Dec. 9, 2016

(65) Prior Publication Data
US 2017/0166592 A1 Jun. 15, 2017

Related U.S. Application Data

(60) Provisional application No. 62/264,919, filed on Dec. 9, 2015.

(51) Int. Cl.
*C07D 401/14* (2006.01)
*A61K 31/437* (2006.01)
*C07D 519/00* (2006.01)
*A61K 31/4545* (2006.01)

(52) U.S. Cl.
CPC .......... *C07D 519/00* (2013.01); *A61K 31/437* (2013.01); *A61K 31/4545* (2013.01)

(58) Field of Classification Search
CPC ........................... C07D 401/14; A61K 31/437
USPC ........................................ 546/119; 514/303
See application file for complete search history.

(56) References Cited

U.S. PATENT DOCUMENTS

| | | | | |
|---|---|---|---|---|
| 6,087,380 A * | 7/2000 | Hauel | ................. | C07D 209/14 514/336 |
| 6,897,207 B2 | 5/2005 | Cox et al. | | |
| 7,001,906 B2 | 2/2006 | Prudhomme et al. | | |
| 8,227,485 B2 | 7/2012 | Poitout et al. | | |

OTHER PUBLICATIONS

Berge et al., "Pharmaceutical Salts," Journal of Pharmaceutical Sciences, vol. 66, No. 1, Jan. 1977 (pp. 1-19).
Brinkmann et al., "Neutrophil extracellular traps kill bacteria," Science vol. 303, No. 5663, Mar. 2004 (pp. 1532-1535).
Chang et al., "Increased PADI4 expression in blood and tissues of patients with malignant tumors," BMC Cancer, vol. 9, No. 40, Jan. 2009 (11 pages).
Cho et al., "Fragment-Based Discovery of 7-Azabenzimidazoles as Potent, Highly Selective, and Orally Active CDK4/6 Inhibitors," ACS Medicinal Chemistry Letters, vol. 3, May 2012 (pp. 445-449).
Chumanevich et al., "Suppression of colitis in mice by Cl-amidine: a novel peptidylarginine deiminase inhibitor," American Journal of Physiology. Gastrointestinal and Liver Physiology, vol. 300, No. 6, Jun. 2011 (pp. G929-G938).
Clark et al., "Platelet TLR4 activates neutrophil extracellular traps to ensnare bacteria in septic blood," Nature Medicine, vol. 13, No. 4, Apr. 2007 (pp. 463-469).
Dworski et al., "Eosinophil and neutrophil extracellular DNA traps in human allergic asthmatic airways," The Journal of Allergy and Clinical Immunology, vol. 127, No. 5, May 2011 (pp. 1260-1266).
Fuchs et al., "Extracellular DNA traps promote thrombosis," The Proceedings of the National Academy of Sciences U.S.A., vol. 107, No. 36, Sep. 2010 (pp. 15880-15885).
Hakkim et al., "Impairment of neutrophil extracellular trap degradation is associated with lupus nephritis," The Proceedings of the National Academy of Sciences U.S.A., vol. 107, No. 21, May 2010 (pp. 9813-9818).
International Search Report and Written Opinion issued by the United States Patent and Trademark Office as International Searching Authority for International Application No. PCT/US2016/065865, dated Feb. 21, 2017 (8 pages).
Jones et al., "Protein arginine deiminase 4(PAD4): Current understanding and future therapeutic potential," Current Opinion in Drug Discovery & Development, vol. 12, No. 5, Sep. 2009 (pp. 616-627).
Kessenbrock et al., "Netting neutrophils in autoimmune small-vessel vasculitis," Nature Medicine, vol. 15, No. 6, Jun. 2009 (pp. 623-625).
Kochi et al., "PADI4 polymorphism predisposes male smokers to rheumatoid arthritis," Annals of the Rheumatic Diseases, vol. 70, No. 3, Mar. 2011 (pp. 512-515).
Lange et al., "Protein deiminases: new players in the developmentally regulated loss of neural regenerative ability," Developmental Biology, vol. 355, No. 2, Jul. 2011 (pp. 205-214).
Li et al., "PAD4 is essential for antibacterial innate immunity mediated by neutrophil extracellular traps," The Journal of Experimental Medicine, vol. 207, No. 9, Aug. 2010 (1853-1862).
Li et al., "Regulation of p53 Target Gene Expression by Peptidylarginine Deiminase 4," Molecular and Cellular Biology, vol. 28, No. 15, Aug. 2008 (pp. 4745-4758).
Lin et al., "Mast cells and neutrophils release IL-17 through extracellular trap formation m psoriasis," The Journal of Immunology, vol. 187, No. 1, Jul. 2011 (pp. 490-500).
Neeli et al., "Histone Deimination as a Response to Inflammatory Stimuli in Neutrophils," The Journal of Immunology, vol. 108, No. 3, Feb. 2008 (pp. 1895-1902).
Savchenko et al., "Long pentraxin 3 (PTX3) expression and release by neutrophils in vitro and in ulcerative colitis," Pathology International, vol. 61, No. 5, May 2011 (pp. 290-297).
Slack et al., "Protein Arginine Deiminase 4: a target for an epigenetic cancer therapy," Cellular and Molecular Life Sciences, vol. 68, No. 4, Feb. 2011 (pp. 709-720).
Villanueva et al., "Netting neutrophils induce endothelial damage, infiltrate tissues, and expose immunostimulatory molecules in systemic lupus erythematosus," The Journal of Immunology, vol. 187, No. 1, Jul. 2011 (pp. 538-552).

(Continued)

*Primary Examiner* — Niloofar Rahmani
(74) *Attorney, Agent, or Firm* — Andrea L. C. Reid; Dechert LLP

(57) ABSTRACT

The present invention provides compounds useful as inhibitors of PAD4, compositions thereof, and methods of treating PAD4-related disorders.

17 Claims, No Drawings

(56) References Cited

OTHER PUBLICATIONS

Vitkov et al., "Neutrophil Fate in Gingival Crevicular Fluid," Ultrastructural Pathology, vol. 34, No. 1, Jan. 2010 (6 pages).
Wegner et al., "Autoimmunity to specific citrullinated proteins gives the first clues to the etiology of rheumatoid arthritis," Immunological Reviews, vol. 233, No. 1, Jan. 2010 (pp. 34-54).
Willis et al., "N-α-Benzoyl-N5-(2-Chloro-1-Iminoethyl)-L-Ornithine Amide, a Protein Arginine Deiminase Inhibitor, Reduces the Severity of Murine Collagen-Induced Arthritis," The Journal of Immunology, vol. 186, No. 7, Apr. 2011 (pp. 4396-4404).

\* cited by examiner

AZA-BENZIMIDAZOLE INHIBITORS OF PAD4

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an auto-immune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2014512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrulllination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R. et al, J. Allergy Clin. Immunol., 127(5), (2011), 1260-6), deep vein thrombosis (Fuchs T et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V. et al, Science, 303, (2004), 1532-5), and stroke. In addition, there is evidence that NETs may contribute to pathology in diseases affecting the skin, eg in cutaneous lupus erythematosis (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formula I are useful as inhibitors of PAD4:

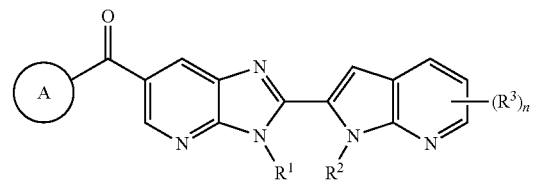

I or a pharmaceutically acceptable salt thereof, wherein each of $R^1$, $R^2$, $R^3$, n and Ring A is as defined and described herein.

It has also been found that compounds of formula I' are useful as inhibitors of PAD4:

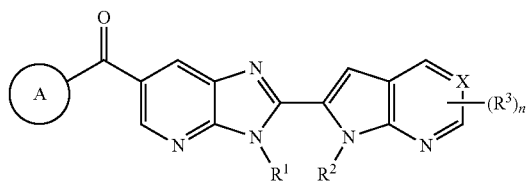

or a pharmaceutically acceptable salt thereof, wherein each of $R^1$, $R^2$, $R^3$, Ring A, X and n is as defined and described herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosis, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. In some embodiments, the present invention provides a compound of formula I:

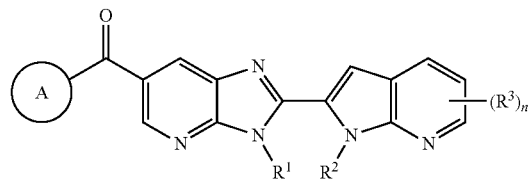

or a pharmaceutically acceptable salt thereof, wherein:
$R^1$ is hydrogen, —CN, —OR, or $C_{1-6}$ aliphatic optionally substituted with 1-4 groups selected from fluorine, —CN, or OR;
$R^2$ is hydrogen or $C_{1-10}$ aliphatic optionally substituted with 1-5 groups selected from fluorine, —CN, or —OR;
Ring A is

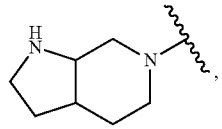 , 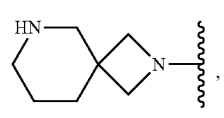 ,

-continued

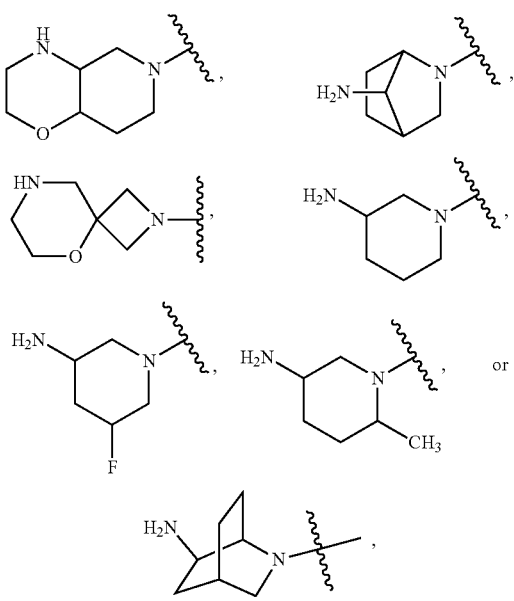

wherein Ring A is optionally substituted with 1-4 groups selected from fluorine, —CN, —OR, or $C_{1-6}$ aliphatic optionally substituted with 1-3 fluorine atoms;
each $R^3$ is independently halogen, —CN, —R, or —OR;
n is 0-3; and
each R is independently hydrogen or $C_{1-6}$ aliphatic optionally substituted with 1-3 fluorine atoms.

In some embodiments, the present invention provides a compound of formula I':

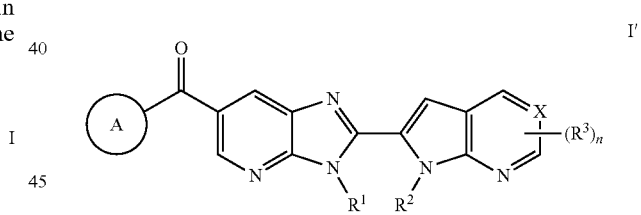

or a pharmaceutically acceptable salt thereof, wherein:
$R^1$ is hydrogen, —CN, —OR,

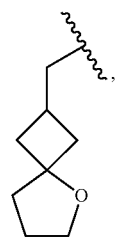 [SMILES: *CC1CC2(CCCO2)C1]

or $C_{1-6}$ aliphatic optionally substituted with 1-4 groups selected from fluorine, —CN, or OR;
$R^2$ is hydrogen or $C_{1-10}$ aliphatic optionally substituted with 1-5 groups selected from fluorine, —CN, or —OR;

Ring A is

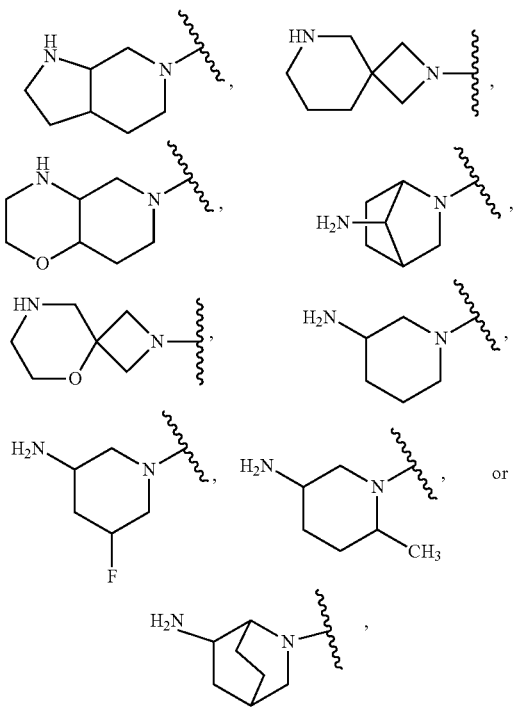

wherein Ring A is optionally substituted with 1-4 groups selected from fluorine, —CN, —OR, or $C_{1-6}$ aliphatic optionally substituted with 1-3 fluorine atoms;
each $R^3$ is independently halogen, —CN, —R, or —OR;
X is C or N;
n is 0-3; and
each R is independently hydrogen or $C_{1-6}$ aliphatic optionally substituted with —OH or 1-3 fluorine atoms.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic," or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$($C_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

3. Description of Exemplary Compounds

According to one aspect, the present invention provides a compound of formula I:

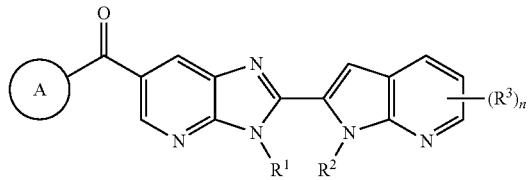

or a pharmaceutically acceptable salt thereof, wherein:
$R^1$ is hydrogen, —CN, —OR, or $C_{1-6}$ aliphatic optionally substituted with 1-4 groups selected from fluorine, —CN, or OR;
$R^2$ is hydrogen or $C_{1-10}$ aliphatic optionally substituted with 1-5 groups selected from fluorine, —CN, or —OR;
Ring A is

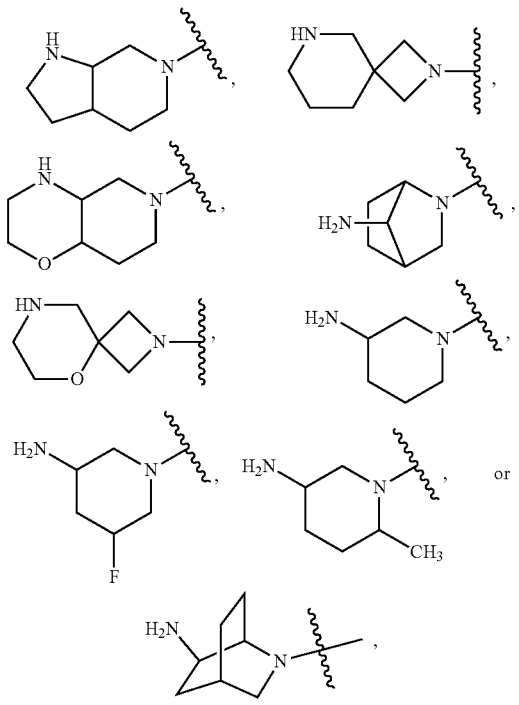

wherein Ring A is optionally substituted with 1-4 groups selected from fluorine, —CN, —OR, or $C_{1-6}$ aliphatic optionally substituted with 1-3 fluorine atoms;

each $R^3$ is independently halogen, —CN, —R, or —OR;

n is 0-3; and each R is independently hydrogen or $C_{1-6}$ aliphatic optionally substituted with 1-3 fluorine atoms.

According to another aspect, the present invention provides a compound of formula I':

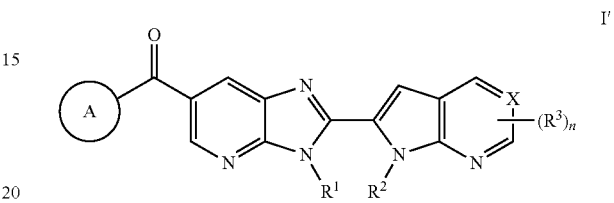

or a pharmaceutically acceptable salt thereof, wherein:
$R^1$ is hydrogen, —CN, —OR,

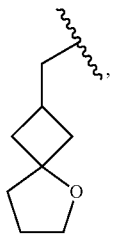 [SMILES: *CC1CC2(CCCO2)C1]

or $C_{1-6}$ aliphatic optionally substituted with 1-4 groups selected from fluorine, —CN, or OR;
$R^2$ is hydrogen or $C_{1-10}$ aliphatic optionally substituted with 1-5 groups selected from fluorine, —CN, or —OR;
Ring A is

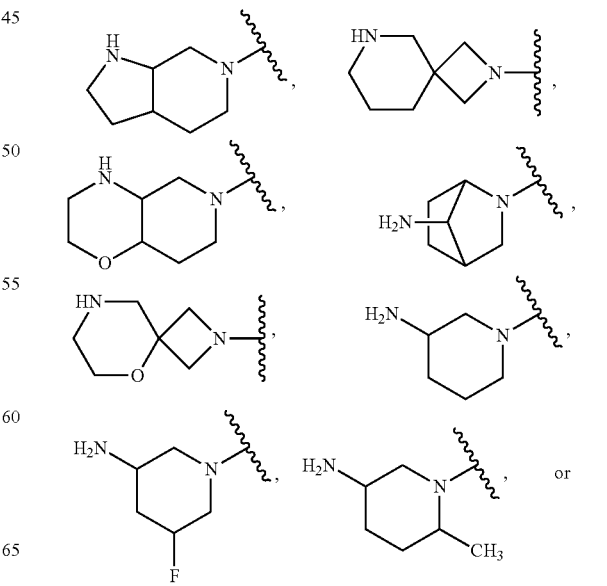

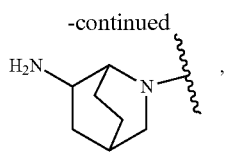

wherein Ring A is optionally substituted with 1-4 groups selected from fluorine, —CN, —OR, or C$_{1-6}$ aliphatic optionally substituted with 1-3 fluorine atoms;
each R$^3$ is independently halogen, —CN, —R, or —OR;
X is C or N;
n is 0-3; and
each R is independently hydrogen or C$_{1-6}$ aliphatic optionally substituted with —OH or 1-3 fluorine atoms.

As defined above and described herein, R$^1$ is hydrogen, —CN, —OR, or C$_{1-6}$ aliphatic optionally substituted with 1-4 groups selected from fluorine, —CN, or —OR. In some embodiments, R$^1$ is hydrogen. In some embodiments, R$^1$ is C$_{1-6}$ aliphatic optionally substituted with 1-4 groups selected from fluorine, —CN, or —OR. In some embodiments, R$^1$ is —CH$_2$CH$_2$OCH$_3$. In some embodiments, R$^1$ is —CN. In some embodiments, R$^1$ is C$_{1-3}$ aliphatic. In some embodiments, R$^1$ is methyl. In some embodiments, R$^1$ is ethyl. In some embodiments, le is propyl. In certain embodiments, R$^1$ is C$_{1-3}$ aliphatic substituted with 1, 2, or 3 fluorine atoms. In some embodiments, R$^1$ is C$_{1-3}$ aliphatic substituted with 2 or 3 fluorine atoms. In some embodiments, R$^1$ is —CH$_2$CHF$_2$. In some embodiments, R$^1$ is

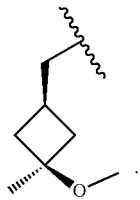

In some embodiments, R$^1$ is

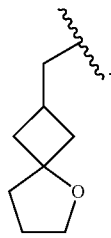 [SMILES: *CC1CC2(CCCO2)C1]

In certain embodiments, R$^1$ is selected from those depicted in Table 1, below.

As defined above and described herein, R$^2$ is hydrogen or C$_{1-10}$ aliphatic optionally substituted with 1-5 groups selected from fluorine, —CN, or —OR. In some embodiments, R$^2$ is hydrogen. In some embodiments, R$^2$ is C$_{1-10}$ aliphatic optionally substituted with 1-5 groups selected from fluorine, —CN, or —OR. In some embodiments, R$^2$ is C$_{1-10}$ aliphatic. In some embodiments, R$^2$ is methyl. In some embodiments, R$^2$ is ethyl. In some embodiments, R$^2$ is propyl. In some embodiments, R$^2$ is butyl. In some embodiments, R$^2$ is pentyl. In some embodiments, R$^2$ is hexyl. In some embodiments, R$^2$ is cyclopropyl. In some embodiments, R$^2$ is cyclobutyl. In some embodiments, R$^2$ is cyclopentyl. In some embodiments, R$^2$ is cyclohexyl. In some embodiments, R$^2$ is cyclopropylmethyl. In some embodiments, R$^2$ is cyclobutylmethyl. In some embodiments, R$^2$ is cyclopentylmethyl. In some embodiments, R$^2$ is cyclohexylmethyl. In some embodiments, R$^2$ is cyclopropylethyl. In some embodiments, R$^2$ is cyclobutylethyl. In some embodiments, R$^2$ is cyclopentylethyl. In some embodiments, R$^2$ is cyclohexylethyl.

In some embodiments, R$^2$ is C$_{1-10}$ aliphatic, optionally substituted with 1-5 fluorine atoms. In some embodiments, R$^2$ is C$_{1-10}$ aliphatic, substituted with 1-5 fluorine atoms. In some embodiments, R$^2$ is C$_{1-10}$ aliphatic, substituted with 1 fluorine atom. In some embodiments, R$^2$ is C$_{1-10}$ aliphatic, substituted with 2 fluorine atoms. In some embodiments, R$^2$ is C$_{1-10}$ aliphatic, substituted with 3 fluorine atoms. In some embodiments, R$^2$ is C$_{1-10}$ aliphatic, substituted with 4 fluorine atoms. In some embodiments, R$^2$ is C$_{1-10}$ aliphatic, substituted with 5 fluorine atoms. In some embodiments, R$^2$ is methyl, substituted with 1-3 fluorine atoms. In some embodiments, R$^2$ is trifluoromethyl. In some embodiments, R$^2$ is ethyl, substituted with 1-5 fluorine atoms. In some embodiments, R$^2$ is 2,2,2-trifluoroethyl. In some embodiments, R$^2$ is —CH$_2$CF$_2$CH$_3$. In some embodiments, R$^2$ is propyl, substituted with 1-5 fluorine atoms. In some embodiments, R$^2$ is 3,3,3-trifluoropropyl. In some embodiments, R$^2$ is butyl, substituted with 1-5 fluorine atoms. In some embodiments, R$^2$ is 4,4,4-trifluorobutyl. In some embodiments, R$^2$ is pentyl, substituted with 1-5 fluorine atoms. In some embodiments, R$^2$ is 5,5,5-trifluoropentyl. In some embodiments, R$^2$ is hexyl, substituted with 1-5 fluorine atoms. In some embodiments, R$^2$ is 6,6,6-trifluorohexyl. In certain embodiments, R$^2$ is selected from those depicted in Table 1, below.

As defined above, each R$^3$ is independently halogen, —CN, —R, or —OR. In some embodiments, R$^3$ is hydrogen. In some embodiments, each R$^3$ is independently halogen or —CN. In some embodiments, R$^3$ is C$_{1-6}$ aliphatic or —OR. In some embodiments, R$^3$ is —OCH$_3$. In some embodiments, R$^3$ is —OCHF$_2$. In some embodiments, R$^3$ is ethyl. In some embodiments, R$^3$ is —CF$_3$. In some embodiments, R$^3$ is —CHF$_2$. In some embodiments, R$^3$ is —C(OH)(CH$_3$)$_2$. In certain embodiments, R$^3$ is selected from those depicted in Table 1, below.

As defined above, Ring A is

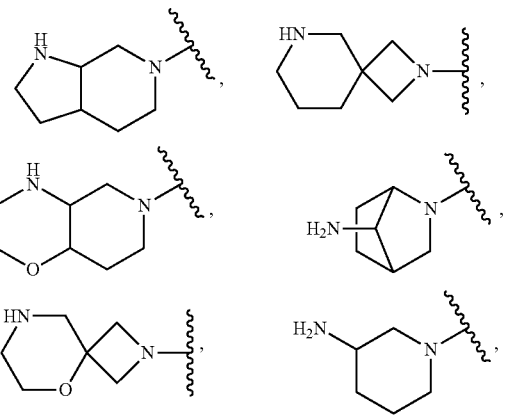

-continued

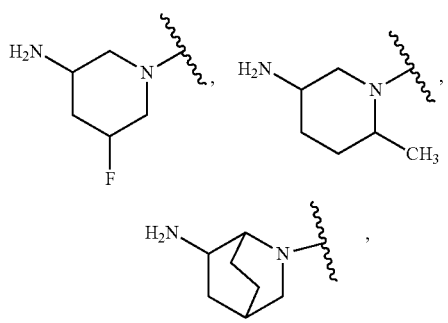

wherein Ring A is optionally substituted with 1-4 groups selected from fluorine, —CN, —OR, or C$_{1-6}$ aliphatic optionally substituted with 1-3 fluorine atoms.

In some embodiments, Ring A is selected from

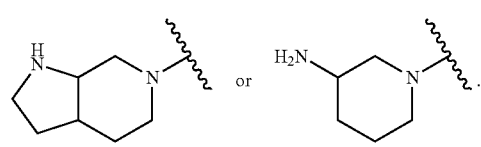 [SMILES: *N1CCC2CCNC2C1 ; *N1CCCC(N)C1]

In some embodiments, Ring A is

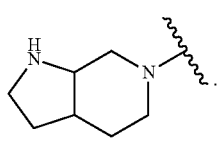 [SMILES: *N1CCC2CCNC2C1]

In some embodiments, Ring A is

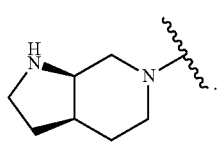

In some embodiments, Ring A is

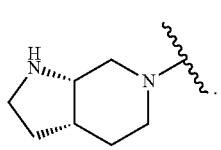

In some embodiments, Ring A is

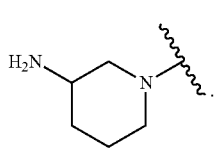 [SMILES: *N1CCC[C@H](N)C1]

In some embodiments, Ring A is

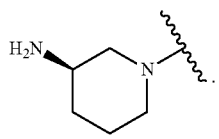

In some embodiments, Ring A is

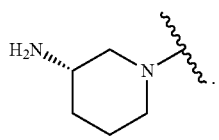

In some embodiments, Ring A is

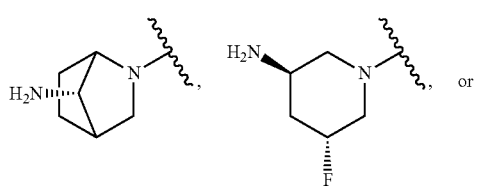

In some embodiments, Ring A is

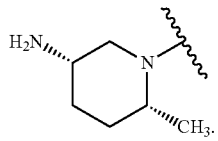

In some embodiments, Ring A is

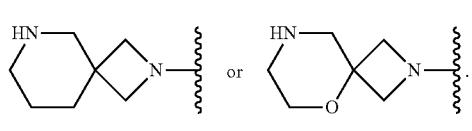

In some embodiments, Ring A is

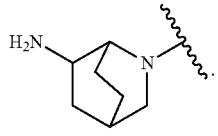

In some embodiments, Ring A is

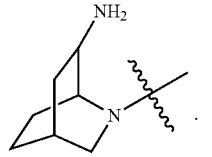 [SMILES: *N1CC2CCC1C(N)C2]

In some embodiments, Ring A is

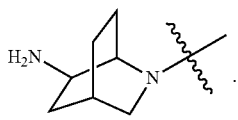

In certain embodiments, Ring A is selected from those depicted in Table 1, below.

In some embodiments, $R^1$ is methyl, $R^2$ is 2,2,2-trifluoroethyl, and Ring A is

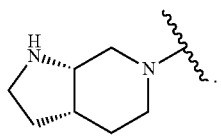 [SMILES: *N1CC[C@@H]2CCN[C@@H]2C1]

In some embodiments, $R^1$ is ethyl, $R^2$ is cyclopropylmethyl, and Ring A is

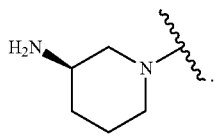 [SMILES: *N1CCC[C@@H](N)C1]

In some embodiments, $R^1$ is methyl, $R^2$ is 2,2,2-trifluoroethyl, and Ring A is

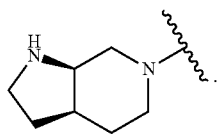 [SMILES: *N1CC[C@H]2CCN[C@H]2C1]

In some embodiments, $R^1$ is ethyl, $R^2$ is ethyl, and Ring A is

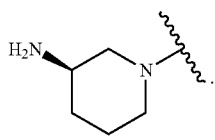

In some embodiments, $R^1$ is methyl, $R^2$ is 2,2,2-trifluoroethyl, and Ring A is

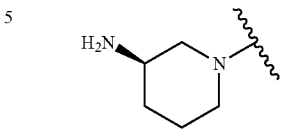

In some embodiments, $R^1$ is methyl, $R^2$ is 2,2,2-trifluoroethyl, and Ring A is

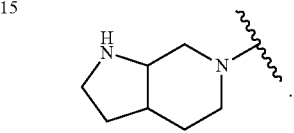

In some embodiments, $R^1$ is methyl, $R^2$ is cyclopropylmethyl, and Ring A is

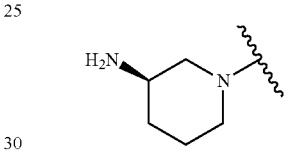

In some embodiments, $R^1$ is methyl, $R^2$ is cyclopropylmethyl, and Ring A is

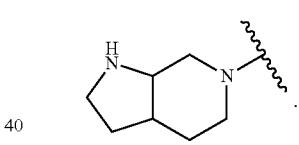

As defined above and described herein, n is 0-3. In some embodiments, n is 0. In some embodiments, n is 1. In some embodiments, n is 2. In some embodiments, n is 3. In certain embodiments, n is selected from those depicted in Table 1, below.

As described herein, X is C or N. In some embodiments, X is C. In some embodiments, X is N. In certain embodiments, X is selected from those depicted in Table 1, below.

In some embodiments, the compound of formula I or formula I' is selected from those depicted below in Table 1.

TABLE 1

Exemplary Compounds of Formula I and Formula I'

I-1
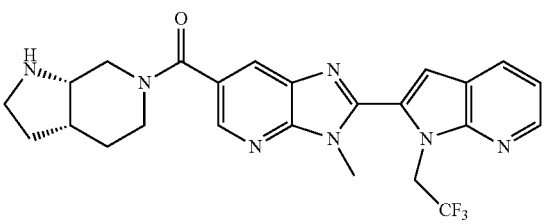 [SMILES: Cn1c(-c2cc3cccnc3n2CC(F)(F)F)nc2cc(C(=O)N3CC[C@@H]4CCN[C@@H]4C3)cnc21]

TABLE 1-continued
Exemplary Compounds of Formula I and Formula I'
I-2
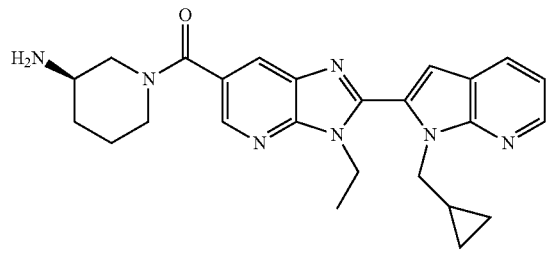 [SMILES: CCn1c(-c2cc3cccnc3n2CC2CC2)nc2cc(C(=O)N3CCC[C@@H](N)C3)cnc21]
I-3
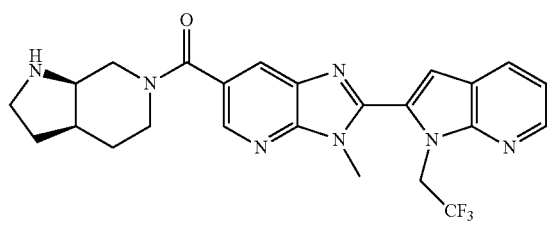 [SMILES: Cn1c(-c2cc3cccnc3n2CC(F)(F)F)nc2cc(C(=O)N3CC[C@H]4CCN[C@H]4C3)cnc21]
I-4
I-5
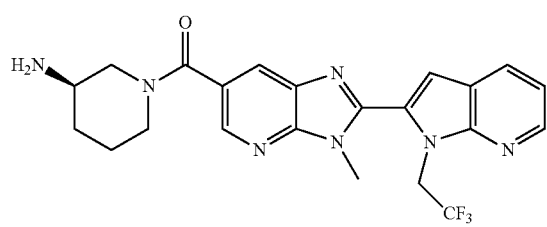 [SMILES: Cn1c(-c2cc3cccnc3n2CC(F)(F)F)nc2cc(C(=O)N3CCC[C@@H](N)C3)cnc21]
I-6
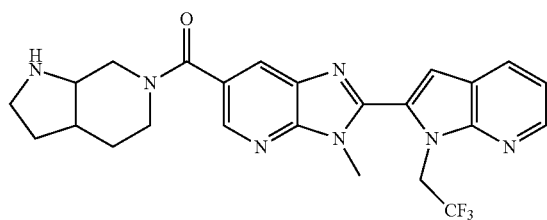 [SMILES: Cn1c(-c2cc3cccnc3n2CC(F)(F)F)nc2cc(C(=O)N3CCC4CCNC4C3)cnc21]
I-7
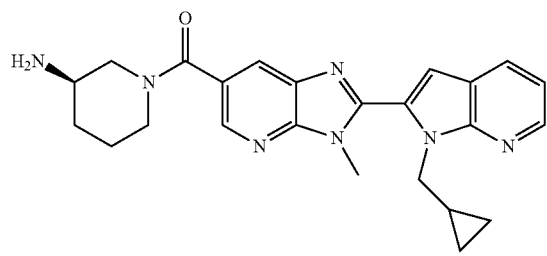 [SMILES: Cn1c(-c2cc3cccnc3n2CC2CC2)nc2cc(C(=O)N3CCC[C@@H](N)C3)cnc21]

TABLE 1-continued
Exemplary Compounds of Formula I and Formula I'
I-8
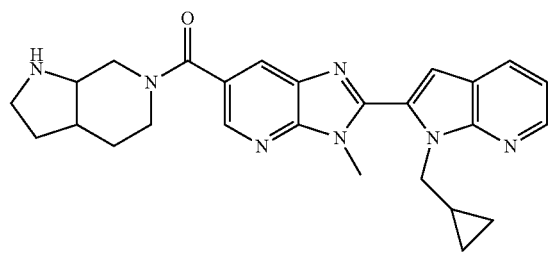 [SMILES: Cn1c(-c2cc3cccnc3n2CC2CC2)nc2cc(C(=O)N3CCC4CCNC4C3)cnc21]
I-9
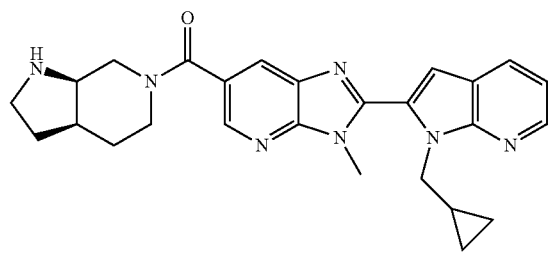 [SMILES: Cn1c(-c2cc3cccnc3n2CC2CC2)nc2cc(C(=O)N3CC[C@H]4CCN[C@H]4C3)cnc21]
I-10
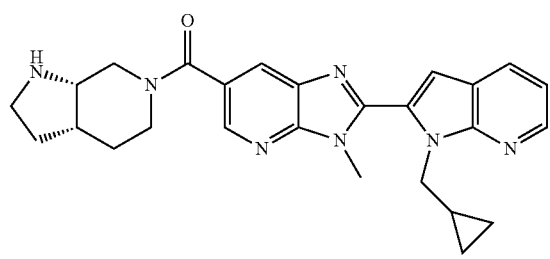 [SMILES: Cn1c(-c2cc3cccnc3n2CC2CC2)nc2cc(C(=O)N3CC[C@@H]4CCN[C@@H]4C3)cnc21]
I-11
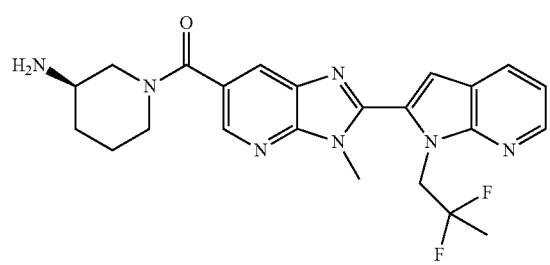 [SMILES: Cn1c(-c2cc3cccnc3n2CC(C)(F)F)nc2cc(C(=O)N3CCC[C@@H](N)C3)cnc21]
I-12
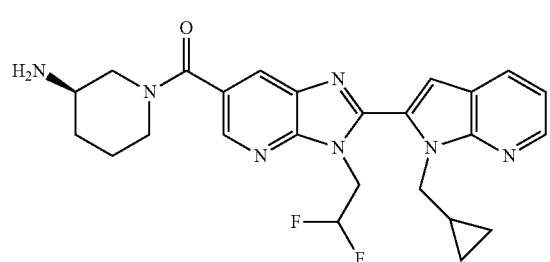
I-13
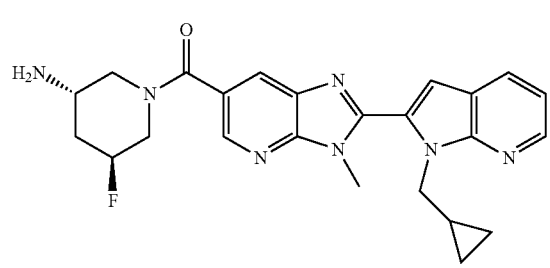 [SMILES: Cn1c(-c2cc3cccnc3n2CC2CC2)nc2cc(C(=O)N3C[C@@H](N)C[C@H](F)C3)cnc21]

TABLE 1-continued
Exemplary Compounds of Formula I and Formula I'
I-14 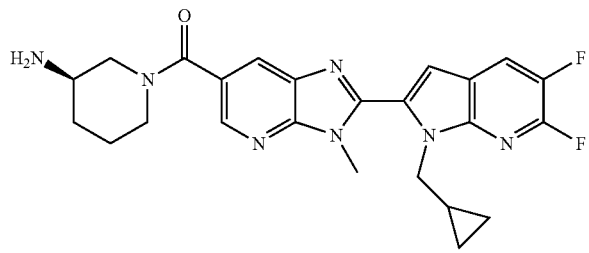 [SMILES: Cn1c(-c2cc3cc(F)c(F)nc3n2CC2CC2)nc2cc(C(=O)N3CCC[C@@H](N)C3)cnc21]
I-15 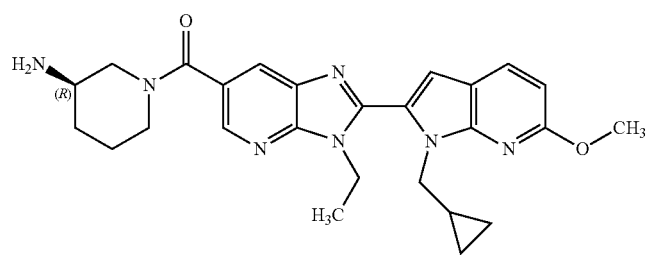
I-16 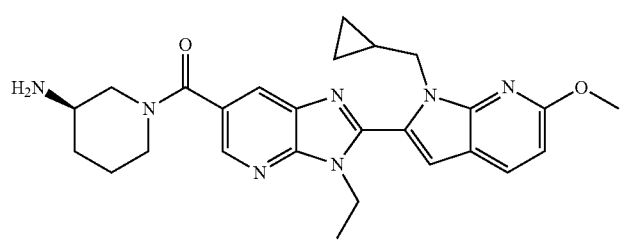 [SMILES: CCn1c(-c2cc3ccc(OC)nc3n2CC2CC2)nc2cc(C(=O)N3CCC[C@@H](N)C3)cnc21]
I-17 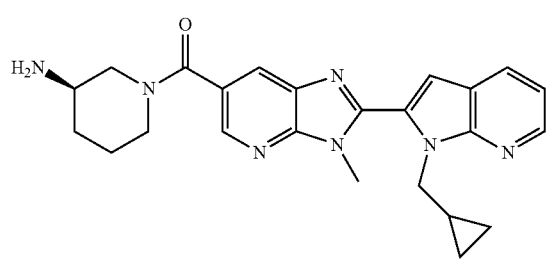
I-18 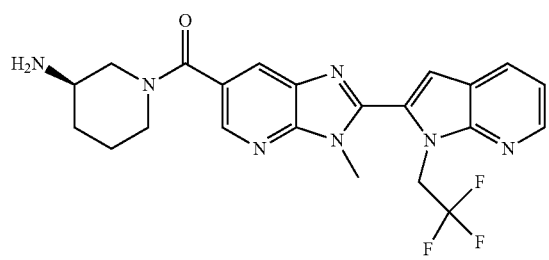 [SMILES: Cn1c(-c2cc3cccnc3n2CC(F)(F)F)nc2cc(C(=O)N3CCC[C@@H](N)C3)cnc21]
I-19 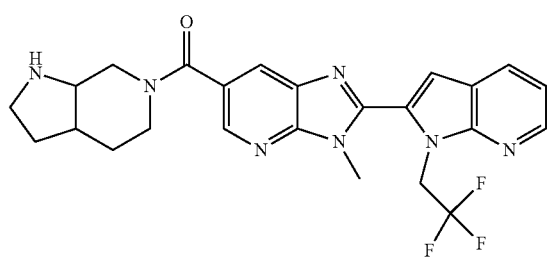 [SMILES: Cn1c(-c2cc3cccnc3n2CC(F)(F)F)nc2cc(C(=O)N3CCC4CCNC4C3)cnc21]

TABLE 1-continued
Exemplary Compounds of Formula I and Formula I'
I-20 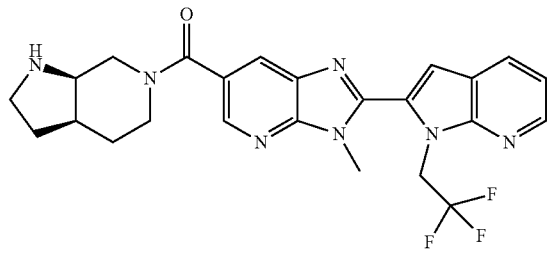 [SMILES: Cn1c(-c2cc3cccnc3n2CC(F)(F)F)nc2cc(C(=O)N3CC[C@H]4CCN[C@H]4C3)cnc21]
I-21 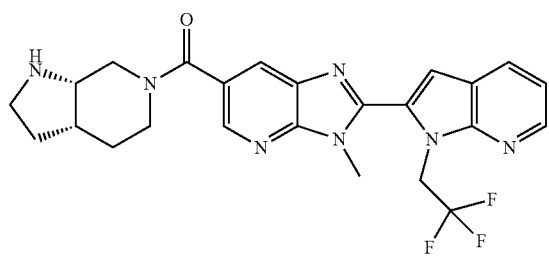 [SMILES: Cn1c(-c2cc3cccnc3n2CC(F)(F)F)nc2cc(C(=O)N3CC[C@@H]4CCN[C@@H]4C3)cnc21]
I-22 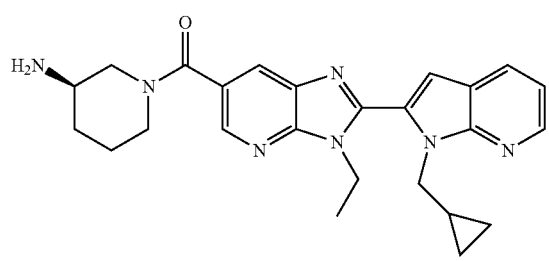 [SMILES: CCn1c(-c2cc3cccnc3n2CC2CC2)nc2cc(C(=O)N3CCC[C@@H](N)C3)cnc21]
I-23 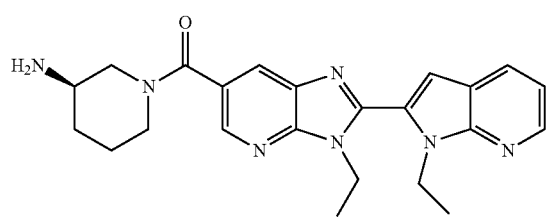 [SMILES: CCn1c(-c2nc3cc(C(=O)N4CCC[C@@H](N)C4)cnc3n2CC)cc2cccnc21]
I-24 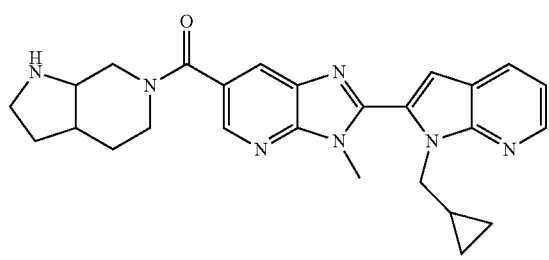 [SMILES: Cn1c(-c2cc3cccnc3n2CC2CC2)nc2cc(C(=O)N3CCC4CCNC4C3)cnc21]
I-25 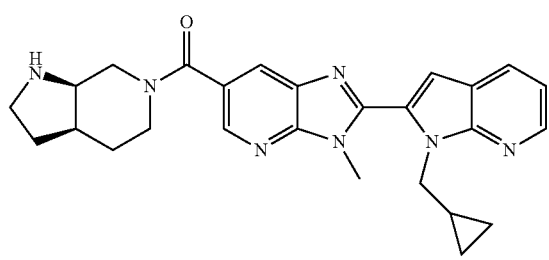 [SMILES: Cn1c(-c2cc3cccnc3n2CC2CC2)nc2cc(C(=O)N3CC[C@H]4CCN[C@H]4C3)cnc21]

TABLE 1-continued
Exemplary Compounds of Formula I and Formula I'
I-26
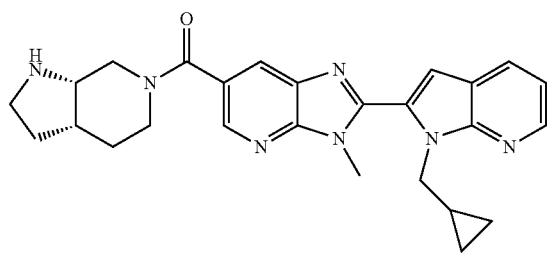 [SMILES: Cn1c(-c2cc3cccnc3n2CC2CC2)nc2cc(C(=O)N3CC[C@@H]4CCN[C@@H]4C3)cnc21]
I-27
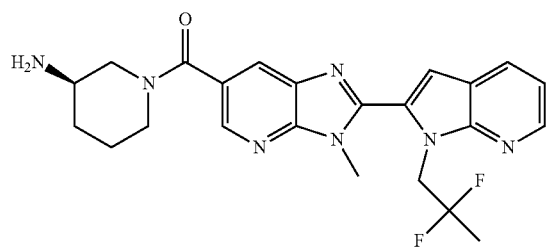
I-28
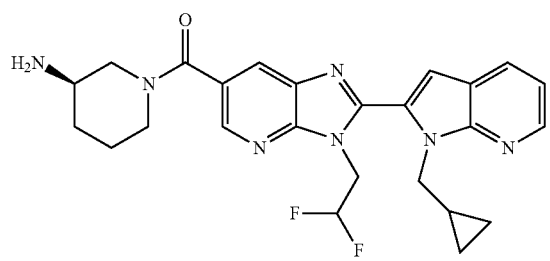 [SMILES: N[C@@H]1CCCN(C(=O)c2cnc3c(c2)nc(-c2cc4cccnc4n2CC2CC2)n3CC(F)F)C1]
I-29
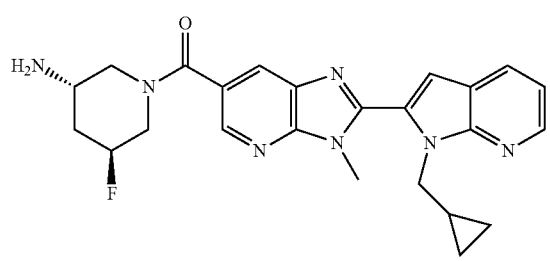 [SMILES: Cn1c(-c2cc3cccnc3n2CC2CC2)nc2cc(C(=O)N3C[C@@H](N)C[C@H](F)C3)cnc21]
I-30
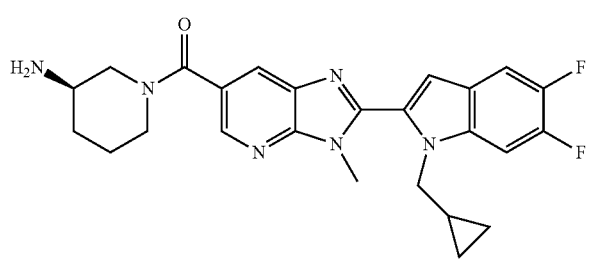 [SMILES: Cn1c(-c2cc3cc(F)c(F)cc3n2CC2CC2)nc2cc(C(=O)N3CCC[C@@H](N)C3)cnc21]
I-31
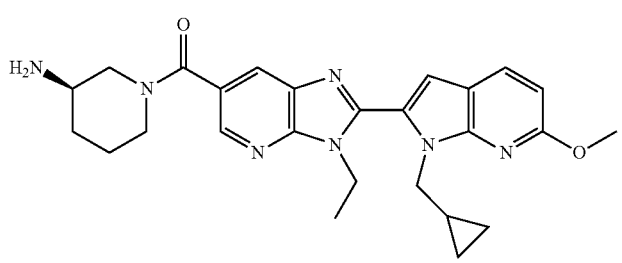 [SMILES: CCn1c(-c2cc3ccc(OC)nc3n2CC2CC2)nc2cc(C(=O)N3CCC[C@@H](N)C3)cnc21]

TABLE 1-continued
Exemplary Compounds of Formula I and Formula I'
I-32
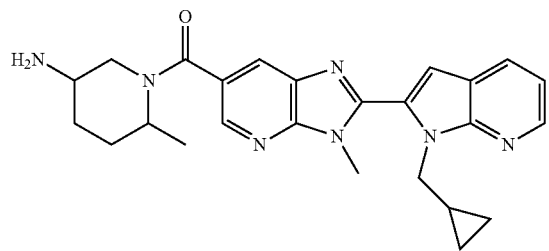 [SMILES: CC1CCC(N)CN1C(=O)c1cnc2c(c1)nc(-c1cc3cccnc3n1CC1CC1)n2C]
I-33
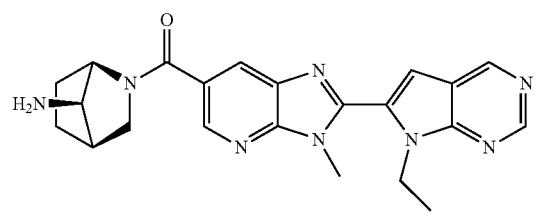 [SMILES: CCn1c(-c2nc3cc(C(=O)N4C[C@H]5CC[C@@H]4[C@@H]5N)cnc3n2C)cc2cncnc21]
I-34
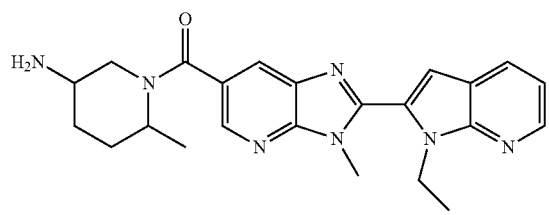 [SMILES: CCn1c(-c2nc3cc(C(=O)N4CC(N)CCC4C)cnc3n2C)cc2cccnc21]
I-35
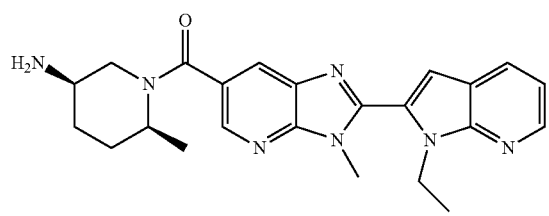 [SMILES: CCn1c(-c2nc3cc(C(=O)N4C[C@H](N)CC[C@@H]4C)cnc3n2C)cc2cccnc21]
I-36
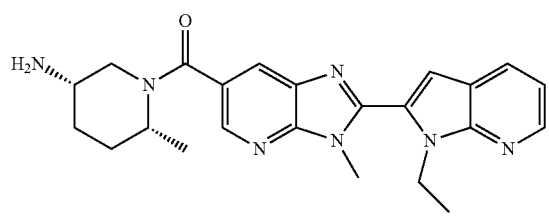 [SMILES: CCn1c(-c2nc3cc(C(=O)N4C[C@@H](N)CC[C@H]4C)cnc3n2C)cc2cccnc21]
I-37
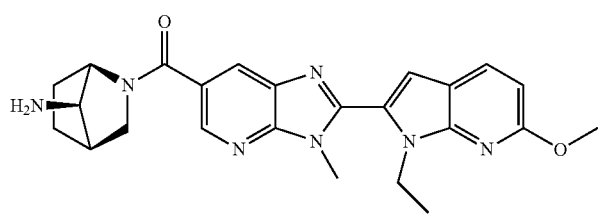 [SMILES: CCn1c(-c2nc3cc(C(=O)N4C[C@H]5CC[C@@H]4[C@@H]5N)cnc3n2C)cc2ccc(OC)nc21]
I-38
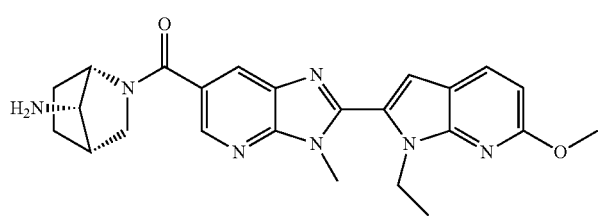 [SMILES: CCn1c(-c2nc3cc(C(=O)N4C[C@@H]5CC[C@H]4[C@H]5N)cnc3n2C)cc2ccc(OC)nc21]

TABLE 1-continued
Exemplary Compounds of Formula I and Formula I'
I-39 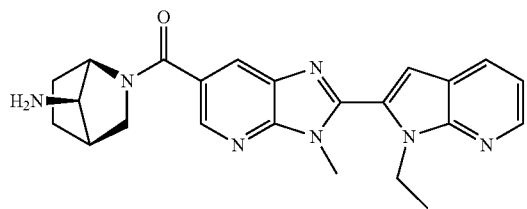 [SMILES: CCn1c(-c2nc3cc(C(=O)N4C[C@H]5CC[C@@H]4[C@@H]5N)cnc3n2C)cc2cccnc21]
I-40 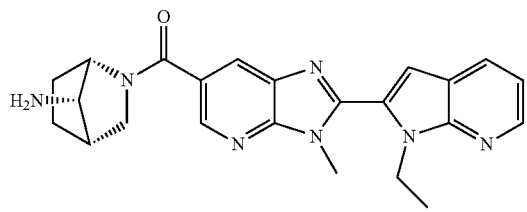 [SMILES: CCn1c(-c2nc3cc(C(=O)N4C[C@@H]5CC[C@H]4[C@H]5N)cnc3n2C)cc2cccnc21]
I-41 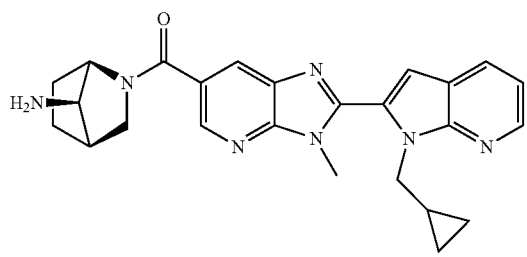 [SMILES: Cn1c(-c2cc3cccnc3n2CC2CC2)nc2cc(C(=O)N3C[C@H]4CC[C@@H]3[C@@H]4N)cnc21]
I-42 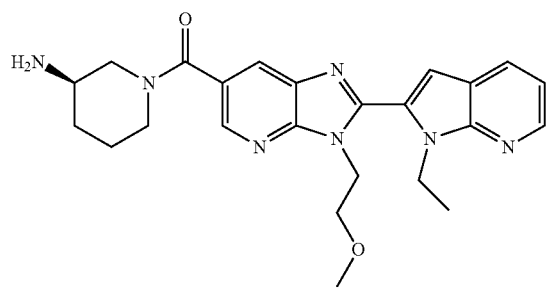 [SMILES: CCn1c(-c2nc3cc(C(=O)N4CCC[C@@H](N)C4)cnc3n2CCOC)cc2cccnc21]
I-43 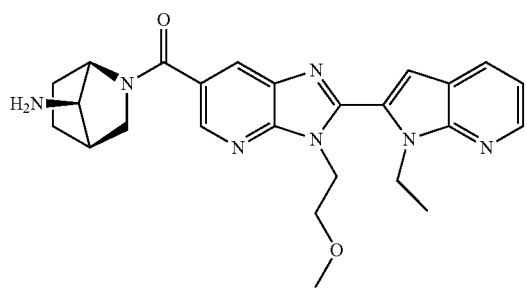 [SMILES: CCn1c(-c2nc3cc(C(=O)N4C[C@H]5CC[C@@H]4[C@@H]5N)cnc3n2CCOC)cc2cccnc21]
I-44 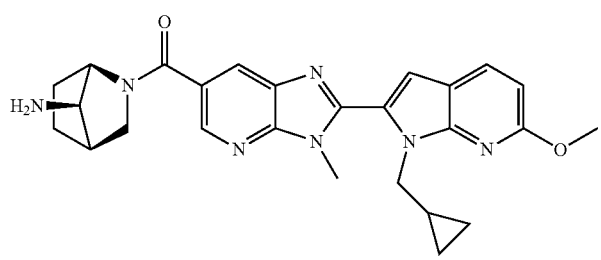 [SMILES: COc1ccc2cc(-c3nc4cc(C(=O)N5C[C@H]6CC[C@@H]5[C@@H]6N)cnc4n3C)n(CC3CC3)c2n1]

TABLE 1-continued
Exemplary Compounds of Formula I and Formula I'
I-45
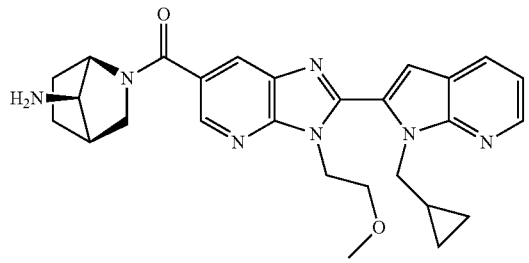 [SMILES: COCCn1c(-c2cc3cccnc3n2CC2CC2)nc2cc(C(=O)N3C[C@H]4CC[C@@H]3[C@@H]4N)cnc21]
I-46
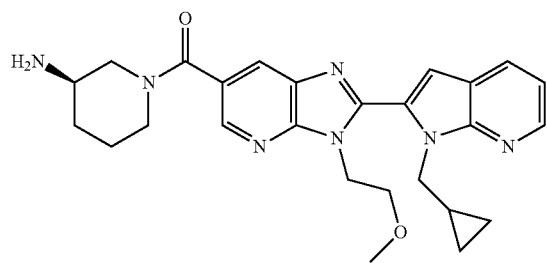 [SMILES: COCCn1c(-c2cc3cccnc3n2CC2CC2)nc2cc(C(=O)N3CCC[C@@H](N)C3)cnc21]
I-47
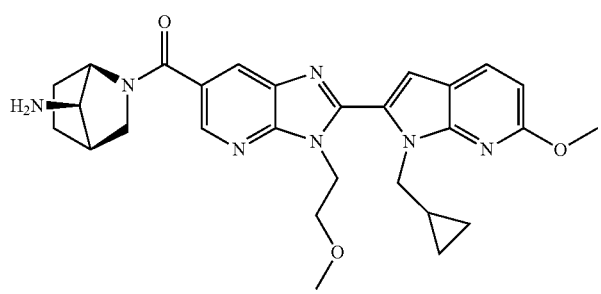 [SMILES: COCCn1c(-c2cc3ccc(OC)nc3n2CC2CC2)nc2cc(C(=O)N3C[C@H]4CC[C@@H]3[C@@H]4N)cnc21]
I-48
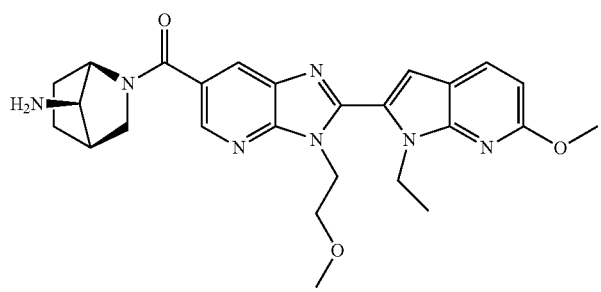 [SMILES: CCn1c(-c2nc3cc(C(=O)N4C[C@H]5CC[C@@H]4[C@@H]5N)cnc3n2CCOC)cc2ccc(OC)nc21]
I-49
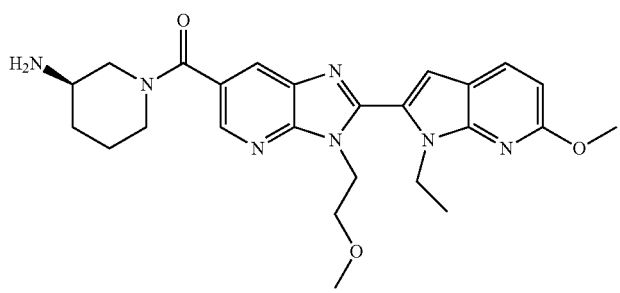 [SMILES: CCn1c(-c2nc3cc(C(=O)N4CCC[C@@H](N)C4)cnc3n2CCOC)cc2ccc(OC)nc21]

TABLE 1-continued
Exemplary Compounds of Formula I and Formula I'
I-50
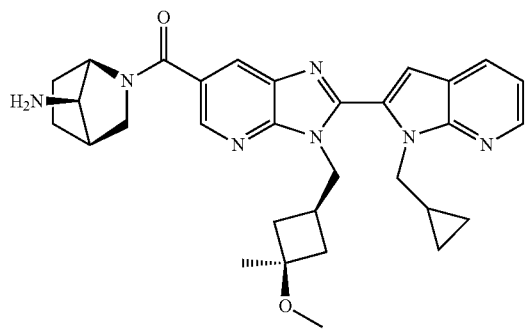 [SMILES: CO[C@]1(C)C[C@H](Cn2c(-c3cc4cccnc4n3CC3CC3)nc3cc(C(=O)N4C[C@H]5CC[C@@H]4[C@@H]5N)cnc32)C1]
I-51
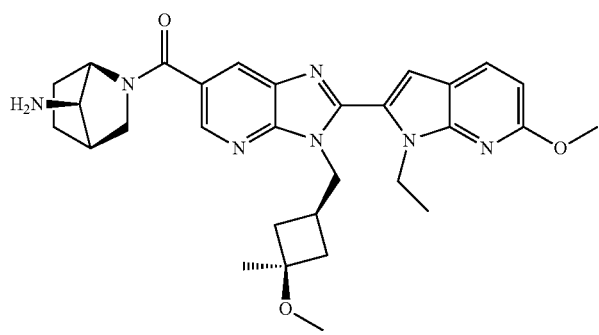 [SMILES: CCn1c(-c2nc3cc(C(=O)N4C[C@H]5CC[C@@H]4[C@@H]5N)cnc3n2C[C@H]2C[C@@](C)(OC)C2)cc2ccc(OC)nc21]
I-52
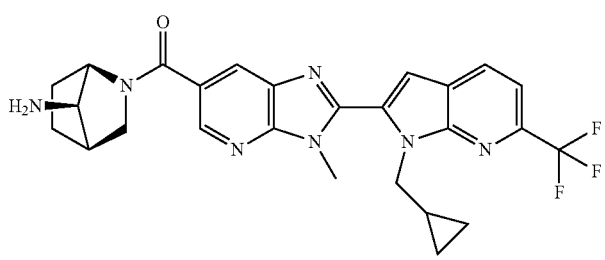 [SMILES: Cn1c(-c2cc3ccc(C(F)(F)F)nc3n2CC2CC2)nc2cc(C(=O)N3C[C@H]4CC[C@@H]3[C@@H]4N)cnc21]
I-53
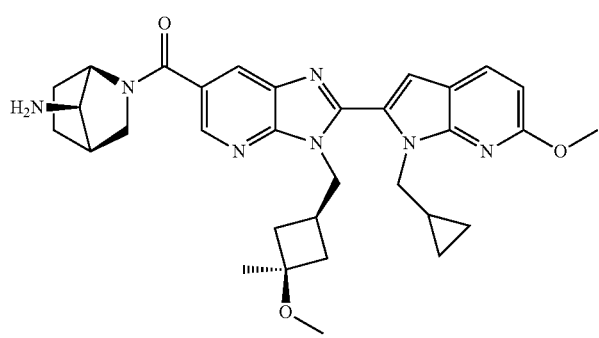 [SMILES: COc1ccc2cc(-c3nc4cc(C(=O)N5C[C@H]6CC[C@@H]5[C@@H]6N)cnc4n3C[C@H]3C[C@@](C)(OC)C3)n(CC3CC3)c2n1]
I-54
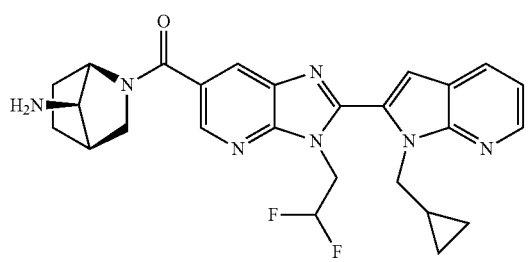 [SMILES: N[C@@H]1[C@@H]2CC[C@H]1N(C(=O)c1cnc3c(c1)nc(-c1cc4cccnc4n1CC1CC1)n3CC(F)F)C2]

TABLE 1-continued
Exemplary Compounds of Formula I and Formula I'
I-55
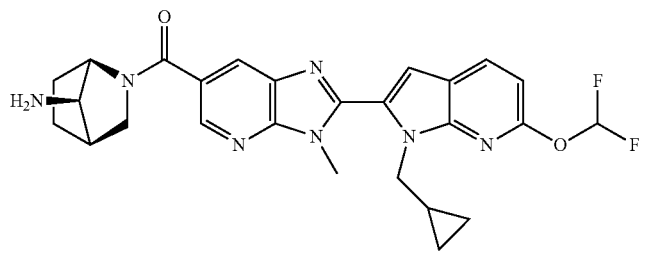 [SMILES: Cn1c(-c2cc3ccc(OC(F)F)nc3n2CC2CC2)nc2cc(C(=O)N3C[C@H]4CC[C@@H]3[C@@H]4N)cnc21]
I-56
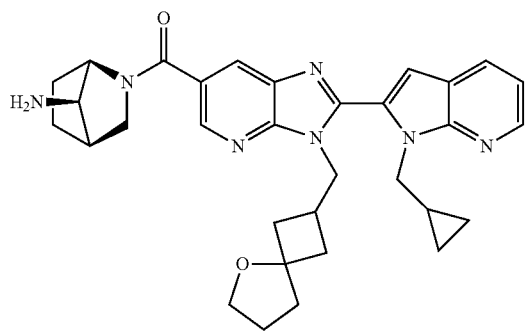 [SMILES: N[C@@H]1[C@@H]2CC[C@H]1N(C(=O)c1cnc3c(c1)nc(-c1cc4cccnc4n1CC1CC1)n3CC1CC3(CCCO3)C1)C2]
I-57
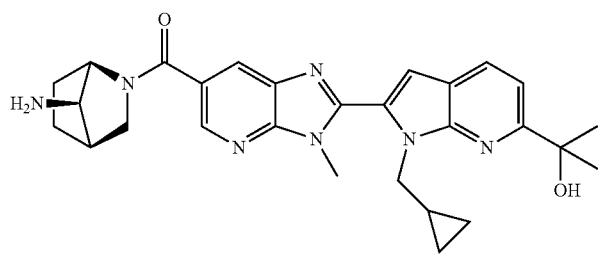 [SMILES: Cn1c(-c2cc3ccc(C(C)(C)O)nc3n2CC2CC2)nc2cc(C(=O)N3C[C@H]4CC[C@@H]3[C@@H]4N)cnc21]
I-58
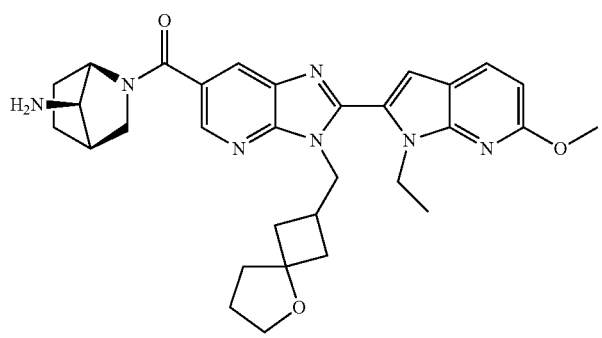 [SMILES: CCn1c(-c2nc3cc(C(=O)N4C[C@H]5CC[C@@H]4[C@@H]5N)cnc3n2CC2CC3(CCCO3)C2)cc2ccc(OC)nc21]
I-59
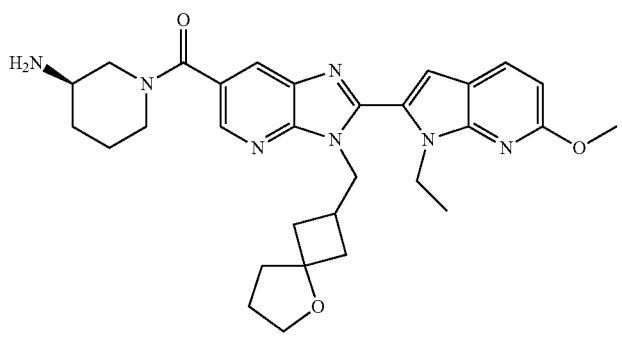 [SMILES: CCn1c(-c2nc3cc(C(=O)N4CCC[C@@H](N)C4)cnc3n2CC2CC3(CCCO3)C2)cc2ccc(OC)nc21]

TABLE 1-continued
Exemplary Compounds of Formula I and Formula I'
I-60
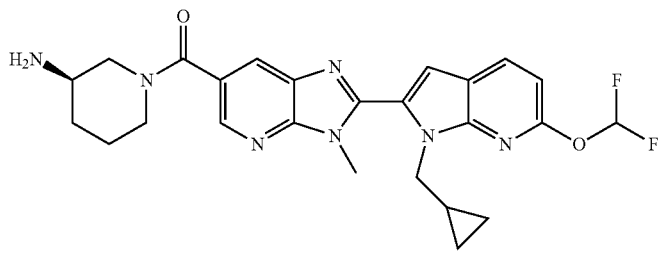 [SMILES: Cn1c(-c2cc3ccc(OC(F)F)nc3n2CC2CC2)nc2cc(C(=O)N3CCC[C@@H](N)C3)cnc21]
I-61
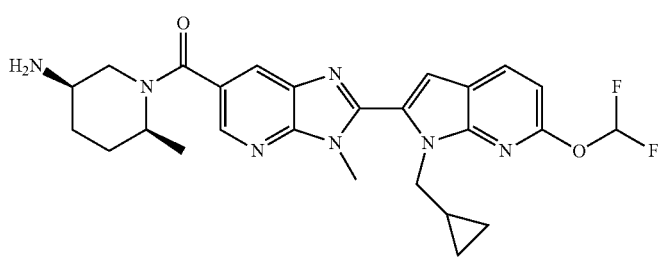 [SMILES: C[C@H]1CC[C@@H](N)CN1C(=O)c1cnc2c(c1)nc(-c1cc3ccc(OC(F)F)nc3n1CC1CC1)n2C]
I-62
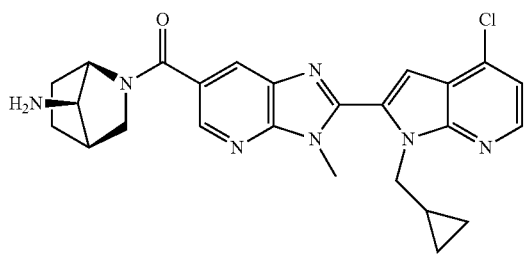 [SMILES: Cn1c(-c2cc3c(Cl)ccnc3n2CC2CC2)nc2cc(C(=O)N3C[C@H]4CC[C@@H]3[C@@H]4N)cnc21]
I-63
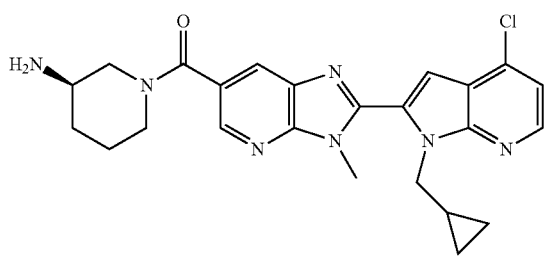 [SMILES: Cn1c(-c2cc3c(Cl)ccnc3n2CC2CC2)nc2cc(C(=O)N3CCC[C@@H](N)C3)cnc21]
I-64
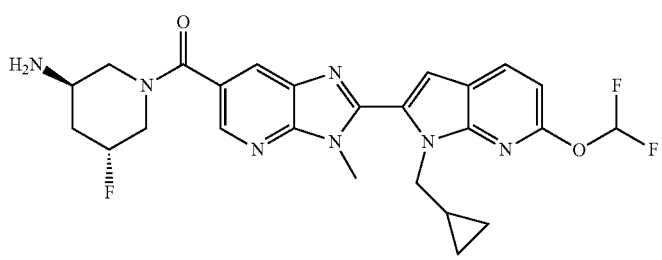 [SMILES: Cn1c(-c2cc3ccc(OC(F)F)nc3n2CC2CC2)nc2cc(C(=O)N3C[C@H](N)C[C@@H](F)C3)cnc21]

In certain embodiments, the present invention provides any compound described above and herein, or a pharmaceutically acceptable salt thereof. In some embodiments, the present invention provides a compound as depicted in Table 1, above, or a pharmaceutically acceptable salt thereof.

In some embodiments, the present invention provides any compound described above and herein in isolated form.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In certain embodiments, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosis, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, behcet's disease, Behcet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osterarthritis, otitis media, paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, and Wegener's granulomatosis.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosis. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosis. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosis comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Analytical LCMS methods:
Method A
MET/u-HPLC (low pH 7 min method)
Column: Phenomenex Kinetex-XB C18, 2.1 mm×100 mm, 1.7 µm
Flow rate: 0.6 ml/min
Mobile Phase: A, Formic acid (aqueous) 0.1% and B, Formic acid (MeCN) 0.1%
Injection Vol: 3 µl
Temp.: 40° C.
Detection: 215 nm (nominal)
Gradient Time (minutes)—% B
  0.00-5
  5.30-100
  5.80-100
  5.82-5
Method B
MET/CR/1600 (high pH 7 min method)
Column: Phenomenex Gemini C18, 2.0 mm×100 mm, 3 µm
Flow rate: 0.5 ml/min
Mobile phase:
  A: 2 mM ammonium bicarbonate in HPLC grade water pH10
  B: HPLC grade MeCN
Injection volume: 3 µl
Temperature: 50° C.

Detection: 215 nm
Gradient time: (minutes)—% B
   0.0-5
   5.50-100
   5.90-100
   5.92-5
   9.00-5
Method C
METCR 1416 (low pH Shimadzu 7 min method)
Column: Waters Atlantis dC18, 2.1 mm×100 mm, 3 μm column
Flow rate: 0.6 ml/min
Mobile Phase: A, Formic acid (aqueous) 0.1% and B, Formic acid (acetonitrile) 0.1%
Injection Vol: 3 μl
Temp.: 40° C.
Detection: 215 nm (nominal)
Gradient Time (minutes)—% B
   0.00-5
   5.00-100
   5.40-100
   5.42-5
Method D
METCR 1410 (low pH Shimadzu 2 min method)
Column: Kinetex Core-Shell C18, 2.1 mm×50 mm, 5 μm column
Flow rate: 1.2 ml/min
Mobile Phase: A, Formic acid (aqueous) 0.1% and B, Formic acid (acetonitrile) 0.1%
Injection Vol: 3 μl
Temp.: 40° C.
Detection: 215 nm (nominal)
Gradient Time (minutes)—% B
   0.00-5
   1.20-100
   1.30-100
   1.31-5
Method E
Chiral HPLC preparative method
Column: Amy-C, 20 mm×250 mm, 5 μm column
Flow rate: 42 ml/min
Mobile Phase: A, Formic acid (aqueous) 0.1% and B, Formic acid (acetonitrile) 0.1%
Injection Vol: 250 μl
Temp.: ambient
Detection: 215 nm (nominal)
Isocratic conditions: 1:1 heptane:IPA (0.1% v/v $NH_3$)
Method F
Chiral purity analysis method
Column: Amy-C, 4.6 mm×250 mm, 5 μm column
Flow Rate: 1 ml/min
Injection Vol: 1.0 μL
Temp.: ambient
Detection: 254 nm
Isocratic Conditions 1:1 heptane:IPA (0.1% v/v $NH_3$)

Compounds of the present invention were prepared according to Scheme 1, below.

Scheme 1

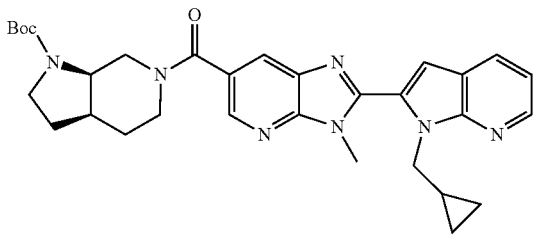

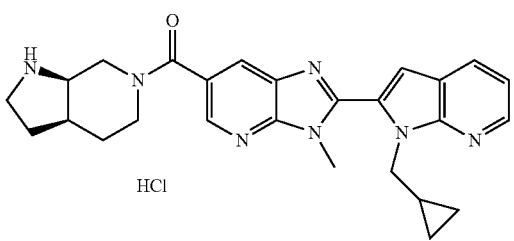

I-9 and $\xrightarrow{\text{HCl}}$ Step 5

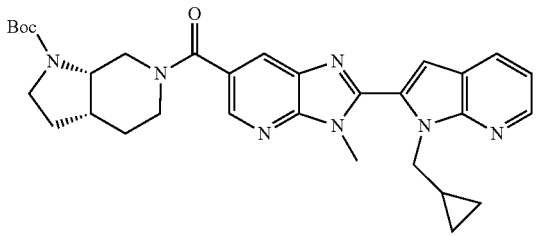

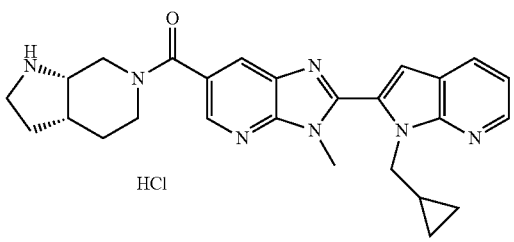

I-10

Synthesis of 2-[1-(cyclopropylmethyl)-1H-pyrrolo[2,3-b]pyridin-2-yl]-3-methyl-6-{octahydro-1H-pyrrolo[2,3-c]pyridine-6-carbonyl}-3H-imidazo[4,5-b]pyridine hydrochloride EV-AT1623-001 (EOAI3440740)

1-(Cyclopropylmethyl)-1H-pyrrolo[2,3-b]pyridine-2-carboxylic acid EV-AQ1977-001—step 1

To a stirred solution of ethyl 1H-pyrrolo[2,3-b]pyridine-2-carboxylate (CAS 221675-35-0, 4.0 g, 21.03 mmol) in DMF (40 ml) at 0° C. was added NaH (60%, 0.95 g, 23.87 mmol) portion wise over 5 min under a nitrogen atmosphere. The resulting mixture was stirred at room temperature for 45 min. (Bromomethyl)cyclopropane (2.45 ml, 25.24 mmol) was added and the reaction mixture was stirred at room temperature for 18 h. The solvent was removed in vacuo and the residue suspended in THF (40 ml). To this mixture was added 5M aqueous sodium hydroxide (20 ml, 100 mmol) and the mixture stirred at 50° C. for 18 h. The solvent was removed in vacuo and the remaining material was acidified with 5M aqueous hydrochloric acid (20 ml) whilst stirring in an ice-bath. The suspension was stirred for 10 min then the precipitate collected by vacuum filtration. The solid was washed with water (2×100 ml) and dried to obtain 3.48 g (76.5%) of 1-(cyclopropylmethyl)-1H-pyrrolo[2,3-b]pyridine-2-carboxylic acid EV-AQ1977-001 as a white powder. LCMS (method D): retention time 1.02 min, M/z=217 (M+1).

Methyl 2-[1-(cyclopropylmethyl)-1H-pyrrolo[2,3-b]pyridin-2-yl]-3-methyl-3H-imidazo[4,5-b]pyridine-6-carboxylate EV-AT1616-001—step 2

To a stirred solution of 1-(cyclopropylmethyl)-1H-pyrrolo[2,3-b]pyridine-2-carboxylic acid (EV-AQ1977-001, 700 mg, 3.24 mmol) in dry DMF (15 ml) were added HATU (1.57 g, 4.05 mmol) and DIPEA (712 μl, 4.05 mmol). The mixture was stirred at room temperature for 2 h before methyl 5-amino-6-(methylamino)pyridine-3-carboxylate (CAS 211915-53-6, 91%, 709 mg, 3.56 mmol) was added and the mixture stirred at room temperature for 16 h and at 50° C. for 4 h. Further methyl 5-amino-6-(methylamino)pyridine-3-carboxylate (91%, 129 mg, 0.65 mmol) was added and stirring at 50° C. was continued for 16 h. The solvent was removed in vacuo the resulting brown oil dissolved in acetic acid (15 ml) and heated at 80° C. for 10 h and at 70° C. for 16 h. The reaction mixture was concentrated under reduced pressure to obtain a brown oil which was purified by flash column chromatography (17-85% EtOAc/heptane) to obtain 650 mg (55.6%) of methyl 2-[1-(cyclopropylmethyl)-1H-pyrrolo[2,3-b]pyridin-2-yl]-3-methyl-3H-imidazo[4,5-b]pyridine-6-carboxylate EV-AT1616-001 as a yellow powder. LCMS (method D): retention time 1.22 min, M/z=362 (M+1).

2-[1-(Cyclopropylmethyl)-1H-pyrrolo[2,3-b]pyridin-2-yl]-3-methyl-3H-imidazo[4,5-b]pyridine-6-carboxylic acid EV-AT1617-001—step 3

To methyl 2-[1-(cyclopropylmethyl)-1H-pyrrolo[2,3-b]pyridin-2-yl]-3-methyl-3H-imidazo[4,5-b]pyridine-6-carboxylate (EV-AT1616-001, 650 mg, 1.80 mmol) in MeOH (20 ml) was added 2M NaOH (10 ml). The mixture was stirred at 50° C. for 3 h. The solvent was removed in vacuo and the resulting cloudy aqueous solution was acidified with 5M HCl (5 ml) whilst stirring. Stirring was continued for 5 min then the precipitate was collected by vacuum filtration, washed with water (2×10 ml) and dried to obtain 610 mg (97.6%) of 2-[1-(cyclopropylmethyl)-1H-pyrrolo[2,3-b]pyridin-2-yl]-3-methyl-3H-imidazo[4,5-b]pyridine-6-carboxylic acid EV-AT1617-001 as a pale yellow powder. LCMS (method D): retention time 1.11 min, M/z=348 (M+1).

Tert-butyl 6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-001—step 4

A stirred solution of 2-[1-(cyclopropylmethyl)-1H-pyrrolo[2,3-b]pyridin-2-yl]-3-methyl-3H-imidazo[4,5-b]pyridine-6-carboxylic acid (EV-AT1617-001, 100 mg, 0.29 mmol) and HATU (126 mg, 0.33 mmol) in DMSO (2.4 ml) and MeCN (1.5 ml) was treated with DIPEA (61 µl, 0.35 mmol) at room temperature. The mixture was stirred for 2 h then tert-butyl octahydro-1H-pyrrolo[2,3-c]pyridine-1-carboxylate (949559-11-9, 72 mg, 0.32 mmol) was added and the reaction mixture stirred for 1.5 h at room temperature. The reaction mixture was diluted with water (0.3 ml) and purified by preparative HPLC (basic method) to obtain 137 mg (84.8%) of tert-butyl 6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-001 as a white powder. LCMS (method D): retention time 1.34 min, M/z=556 (M+1).

2-[1-(Cyclopropylmethyl)-1H-pyrrolo[2,3-b]pyridin-2-yl]-3-methyl-6-{octahydro-1H-pyrrolo[2,3-c]pyridine-6-carbonyl}-3H-imidazo[4,5-b]pyridine EV-AT1623-001 (EOAI3440740)—step 5

1.25M HCl in EtOH (0.5 ml) was added to a solution of tert-butyl 6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate (EV-AT1622-001, 99%, 20 mg, 0.04 mmol) in EtOH (1 ml). The reaction mixture was stirred at 50° C. for 4 h then concentrated to a white residue under reduced pressure. This material was freeze-dried from water (3 ml) to obtain 20.8 mg (quantitative) of 2-[1-(cyclopropylmethyl)-1H-pyrrolo[2,3-b]pyridin-2-yl]-3-methyl-6-{octahydro-1H-pyrrolo[2,3-c]pyridine-6-carbonyl}-3H-imidazo[4,5-b]pyridine hydrochloride EV-AT1623-001 as a yellow powder. LCMS (method A): retention time 1.79 min, M/z=456 (M+1).

Chiral HPLC to obtain tert-butyl (3aS,7aR)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-002 and tert-butyl (3aR,7aS)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-003—step 6

111 mg of tert-butyl 6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-001 were dissolved to 14 mg/mL in methanol and then purified by chiral HPLC (method E) to obtain 48.4 mg (87.2%) of tert-butyl (3aS,7aR)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-002 (absolute stereochemistry arbitrarily assigned) as a white powder and 48.4 mg (87.2%) of tert-butyl (3aR,7aS)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate EV-AT1622-003 (absolute stereochemistry arbitrarily assigned) as a white powder.

EV-AT1622-002 Enantiomeric excess: 97.9, retention time: 7.99 min (method F), LCMS (method A): retention time 3.51 min, M/z=556 (M+1).

EV-AT1622-003 Enantiomeric excess: 96.9, retention time: 9.92 min (method F), LCMS (method A): retention time 3.51 min, M/z=556 (M+1).

6-[(3aR,7aR)-Octahydro-1H-pyrrolo[2,3-c]pyridine-6-carbonyl]-2-[1-(cyclopropylmethyl)-1H-pyrrolo[2,3-b]pyridin-2-yl]-3-methyl-3H-imidazo[4,5-b]pyridine EV-AT1627-001 (EOAI3441172, absolute stereochemistry arbitrarily assigned)—step 5

Tert-butyl (3aS,7aR)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate (EV-AT1622-002, 45 mg, 0.08 mmol) was treated as in step 5, Scheme 1 to obtain 33.9 mg (84.2%) of 6-[(3aR,7aR)-octahydro-1H-pyrrolo[2,3-c]pyridine-6-carbonyl]-2-[1-(cyclopropylmethyl)-1H-pyrrolo[2,3-b]pyridin-2-yl]-3-methyl-3H-imidazo[4,5-b]pyridine hydrochloride EV-AT1627-001 as a yellow powder. LCMS (method A): retention time 1.77 min, M/z=456 (M+1).

6-[(3aS,7aS)-Octahydro-1H-pyrrolo[2,3-c]pyridine-6-carbonyl]-2-[1-(cyclopropylmethyl)-1H-pyrrolo[2,3-b]pyridin-2-yl]-3-methyl-3H-imidazo[4,5-b]pyridine EV-AT1628-001 (EOAI3441173, absolute stereochemistry arbitrarily assigned)—step 5

Tert-butyl (3aR,7aS)-6-{2-[1-(cyclopropylmethyl)-1H-pyrrolo[2,3-b]pyridin-2-yl]-3-methyl-3H-imidazo[4,5-b]pyridine-6-carbonyl}-octahydro-1H-pyrrolo[2,3-c]pyridine-1-carboxylate (EV-AT1622-003, 45 mg, 0.08 mmol) was treated as in step 5, Scheme 1 to obtain 35.1 mg (87.2%) of 6-[(3aS,7aS)-octahydro-1H-pyrrolo[2,3-c]pyridine-6-carbonyl]-2-[1-(cyclopropylmethyl)-1H-pyrrolo[2,3-b]pyridin-2-yl]-3-methyl-3H-imidazo[4,5-b]pyridine hydrochloride EV-AT1628-001 as a yellow powder. LCMS (method A): retention time 1.79 min, M/z=456 (M+1).

(1R,4R,7R)-2-{2-[1-(cyclopropylmethyl)-6-(difluoromethoxy)-1H-pyrrolo[2,3-b]pyridin-2-yl]-3-methyl-3H-imidazo[4,5-b]pyridine-6-carbonyl}-2-azabicyclo[2.2.1]heptan-7-amine EV-AY5721-002 (EOAI3470057, PLK-001205)

Synthesised according to the procedures described in Scheme 1 via synthesis of methyl 1-(cyclopropylmethyl)-6-(difluoromethoxy)-1H-pyrrolo[2,3-b]pyridine-2-carboxylate EV-AY2833-002 as described in Scheme 1.1:

Scheme 1.1

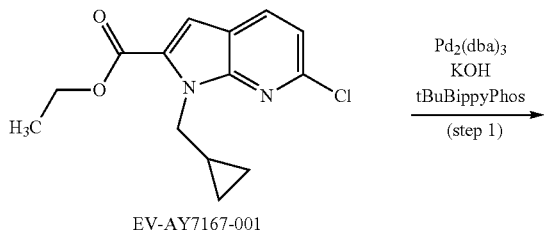

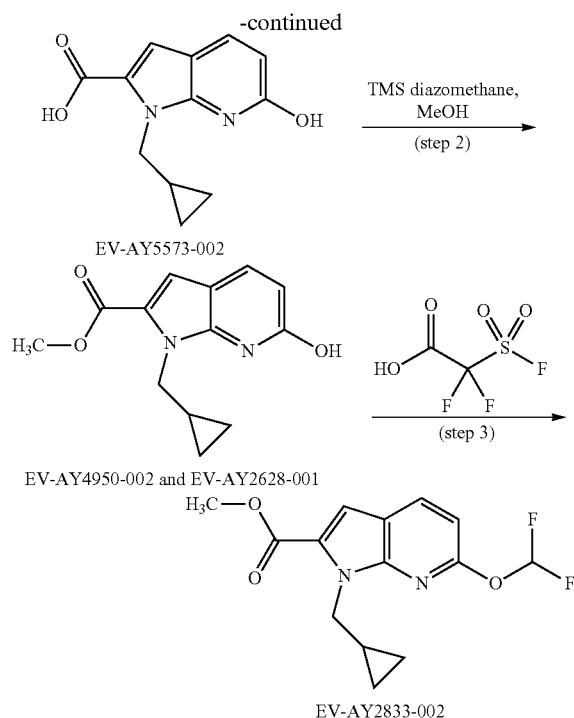

1-(Cyclopropylmethyl)-6-hydroxy-1H-pyrrolo[2,3-b]pyridine-2-carboxylic acid EV-AX5573-002—step 1

Ethyl 6-chloro-1-(cyclopropylmethyl)-1H-pyrrolo[2,3-b]pyridine-2-carboxylate (EV-AY7167-001 synthesised according to Scheme 1, 90%, 1.45 g, 4.68 mmol), Pd$_2$(dba)$_3$ (214 mg, 0.23 mmol), $^t$Bu-BippyPhos (237 mg, 0.47 mmol) and potassium hydroxide (788 mg, 14.0 mmol) were combined in dioxane (7.0 ml) and water (7.0 ml) in a pressure tube. The reaction mixture was purged with nitrogen for 5 minutes then the vessel was sealed and heated at 70° C. for 1.5 h. The reaction mixture was allowed to cool to room temperature then filtered through glass fibre filter paper. The filtrate was diluted with water (10 ml) and extracted with EtOAc (30 ml). The aqueous layer was acidified to pH 5 with 2M HCl and the resulting precipitate filtered and dried to obtain 0.80 g (62.2%) of 1-(cyclopropylmethyl)-6-hydroxy-1H-pyrrolo[2,3-b]pyridine-2-carboxylic acid EV-AX5573-002 as an off-white powder. LCMS (method D): retention time 0.95 min, M/z=233 (M+1).

Methyl 1-(cyclopropylmethyl)-6-hydroxy-1H-pyrrolo[2,3-b]pyridine-2-carboxylate EV-AY4950-002—step 2

2M (Diazomethyl)(trimethyl)silane (1729 μl in diethylether) was added to a stirred suspension of 1-(cyclopropylmethyl)-6-hydroxy-1H-pyrrolo[2,3-b]pyridine-2-carboxylic acid (EV-AX5573-002, 73%, 550 mg, 1.73 mmol) in anhydrous toluene (6.0 ml) and methanol (anhydrous, 2.0 ml, 49.44 mmol) under an atmosphere of nitrogen. The resulting mixture was stirred at room temperature for 1.5 h. Acetic acid (0.70 ml) was added until the bright yellow colour disappeared. The reaction mixture was concentrated in vacuo and triturated with DCM (5 ml). The solid was filtered off under vacuum and dried to afford 131 mg (28.1%) of 1-(cyclopropylmethyl)-6-hydroxy-1H-pyrrolo[2,3-b]pyridine-2-carboxylic acid EV-AY4950-001 as a pale beige solid. LCMS (method D): retention time 1.13 min, M/z=247 (M+1).

Methyl 1-(cyclopropylmethyl)-6-(difluoromethoxy)-1H-pyrrolo[2,3-b]pyridine-2-carboxylate EV-AY2833-002—step 3

To a stirred suspension of methyl 1-(cyclopropylmethyl)-6-hydroxy-1H-pyrrolo[2,3-b]pyridine-2-carboxylate (EV-AY2828-001 synthesised according to steps 1 and 2, 672 mg, 2.73 mmol) in acetonitrile (15.0 ml) was added 2,2-difluoro-2-(fluorosulfonyl)acetic acid (0.71 ml, 6.82 mmol) and the reaction mixture was stirred at room temperature for 2 h. The reaction mixture was filtered and the filtrate was concentrated in vacuo. The crude residue was purified by flash column chromatography (0-100% EtOAc/heptane) to obtain 450 mg (55.7%) of methyl 1-(cyclopropylmethyl)-6-(difluoromethoxy)-1H-pyrrolo[2,3-b]pyridine-2-carboxylate EV-AY2833-002 as an off-white solid. LCMS (method D): retention time 1.39 min, M/z=297 (M+1).

2-(2-{6-[(1R,4R,7R)-7-Amino-2-azabicyclo[2.2.1]heptane-2-carbonyl]-3-methyl-3H-imidazo[4,5-b]pyridin-2-yl}-1-(cyclopropylmethyl)-1H-pyrrolo[2,3-b]pyridin-6-yl)propan-2-ol EV-AY7152-001 (EOAI3476164, PLK-001296)

Synthesised according to the procedures described in Scheme 1 via synthesis of methyl 1-(cyclopropylmethyl)-6-(2-hydroxypropan-2-yl)-1H-pyrrolo[2,3-b]pyridine-2-carboxylate EV-AW6273-002 as described in Scheme 1.2:

Scheme 1.2

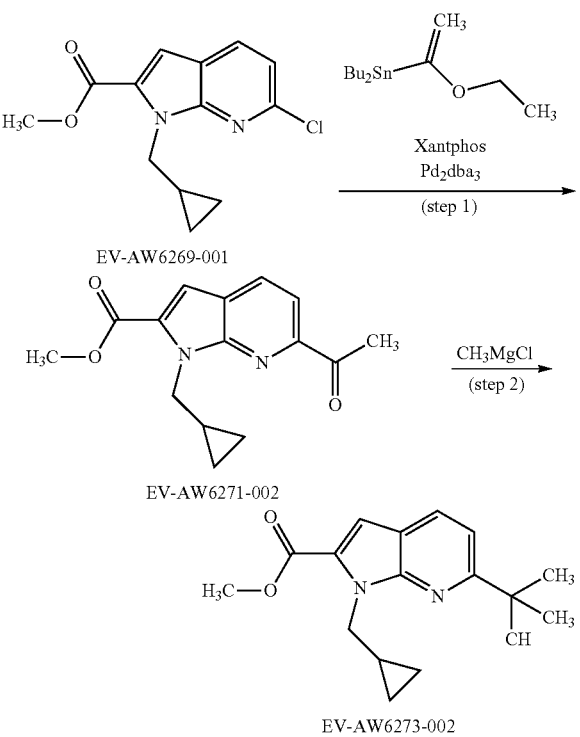

Methyl 6-acetyl-1-(cyclopropylmethyl)-1H-pyrrolo[2,3-b]pyridine-2-carboxylate EV-AW6271-002— step 1

To a solution of methyl 6-chloro-1-(cyclopropylmethyl)-1H-pyrrolo[2,3-b]pyridine-2-carboxylate (EV-AW6269-001, 90%, 1.16 g, 3.93 mmol) in anhydrous dioxane (3 ml) were added tributyl(1-ethoxyethenyl)stannane (1.59 ml, 4.71 mmol), Xantphos (0.17 g, 0.29 mmol) and Pd$_2$dba$_3$ (0.09 g, 0.10 mmol). The reaction mixture was stirred at 90° C. for 17 h. The solvent was removed in vacuo and 1M HCl (50 ml) and DCM (50 ml) were added to the residue. The biphasic mixture was stirred for 20 minutes then the organic layer was separated and concentrated in vacuo. The crude residue was purified by flash column chromatography (0-10% EtOAc/heptane) to obtain 0.512 g (47%) of methyl 6-acetyl-1-(cyclopropylmethyl)-1H-pyrrolo[2,3-b]pyridine-2-carboxylate EV-AW6271-002 as an off-white solid. LCMS (method D): retention time 1.40 min, M/z=273 (M+1).

Methyl 1-(cyclopropylmethyl)-6-(2-hydroxypropan-2-yl)-1H-pyrrolo[2,3-b]pyridine-2-carboxylate EV-AW6273-002—step 2

Methylmagnesium chloride (3M in THF, 642 µl) was added dropwise to a stirred solution of methyl 6-acetyl-1-(cyclopropylmethyl)-1H-pyrrolo[2,3-b]pyridine-2-carboxylate (EV-AW6271-002, 510 mg, 1.84 mmol) in dry THF (5 mL) at −78° C. The reaction was stirred at −78° C. for 2.5 h. Further methylmagnesium chloride (3M in THF, 61 µl) was added at −78° C. and stirring was continued for 30 minutes. The reaction was quenched with water (20 ml) and THF was removed in vacuo. 1M HCl was added to the aqueous layer until pH 3. The aqueous layer was extracted with EtOAc (2×30 ml). The combined extracts dried over sodium sulfate, filtered and concentrated in vacuo. The crude residue was purified by flash column chromatography (0-35% EtOAc/heptane) to obtain 410 mg (76%) of methyl 1-(cyclopropylmethyl)-6-(2-hydroxypropan-2-yl)-1H-pyrrolo[2,3-b]pyridine-2-carboxylate EV-AW6273-002 as an off-white solid. LCMS (method D): retention time 1.23 min, M/z=289 (M+1).

The following compounds were synthesised according to Scheme 1, Scheme 1.1, Scheme 1.2 and procedures described above:

| Structure | # | Mol Wt | LCMS T$_{ret}$ | M/Z(+) | LCMS Method | Salt | Salt Stoichiometry |
|---|---|---|---|---|---|---|---|
| 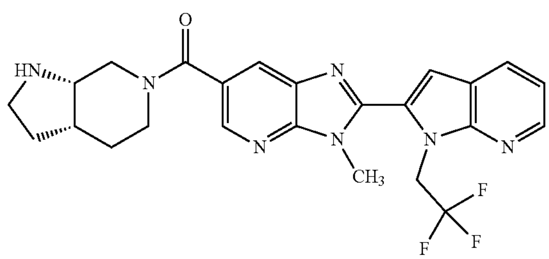 [SMILES: Cn1c(-c2cc3cccnc3n2CC(F)(F)F)nc2cc(C(=O)N3CC[C@@H]4CCN[C@@H]4C3)cnc21] | I-1 | 483.489 | 1.82 min | 484 | A | N/A | N/A |
| 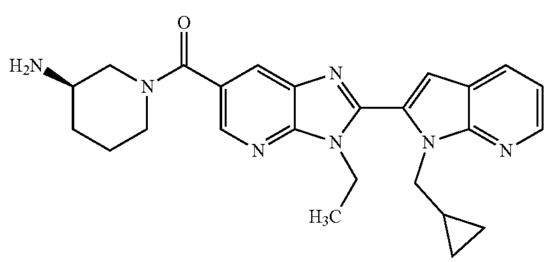 [SMILES: CCn1c(-c2cc3cccnc3n2CC2CC2)nc2cc(C(=O)N3CCC[C@@H](N)C3)cnc21] | I-2 | 443.544 | 1.88 min | 444 | A | HCl | 1 |
| 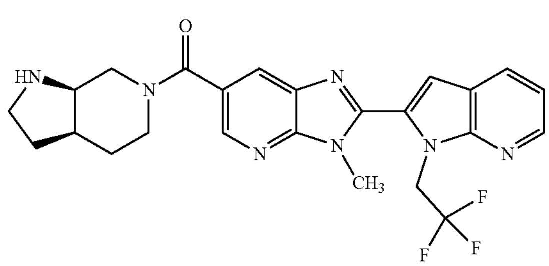 [SMILES: Cn1c(-c2cc3cccnc3n2CC(F)(F)F)nc2cc(C(=O)N3CC[C@H]4CCN[C@H]4C3)cnc21] | I-3 | 483.489 | 1.82 min | 484 | A | N/A | N/A |

-continued

| Structure | # | Mol Wt | LCMS T$_{ret}$ | M/Z(+) | LCMS Method | Salt | Salt Stoichiometry |
|---|---|---|---|---|---|---|---|
| 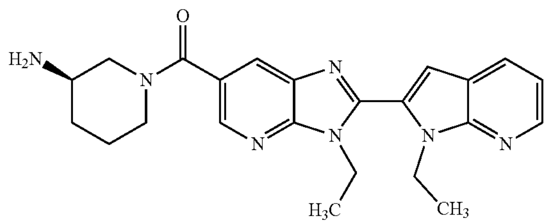 [SMILES: CCn1c(-c2nc3cc(C(=O)N4CCC[C@@H](N)C4)cnc3n2CC)cc2cccnc21] | I-4 | 417.507 | 1.68 min | 418 | A | HCl | 1 |
| 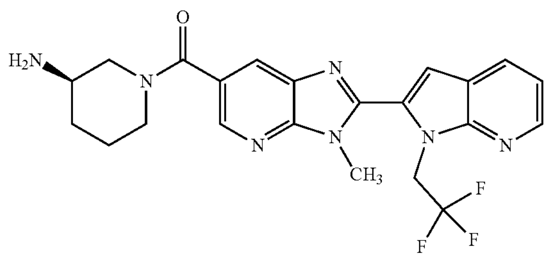 [SMILES: Cn1c(-c2cc3cccnc3n2CC(F)(F)F)nc2cc(C(=O)N3CCC[C@@H](N)C3)cnc21] | I-5 | 457.452 | 1.78 min | 458 | A | N/A | N/A |
| 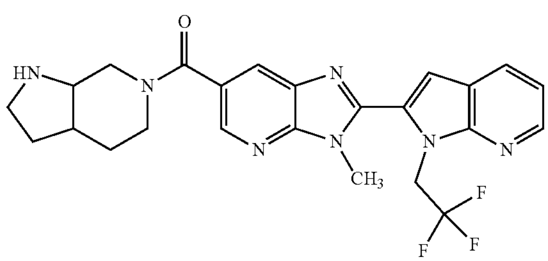 [SMILES: Cn1c(-c2cc3cccnc3n2CC(F)(F)F)nc2cc(C(=O)N3CCC4CCNC4C3)cnc21] | I-6 | 483.489 | 1.81 min | 484 | A | N/A | N/A |
| 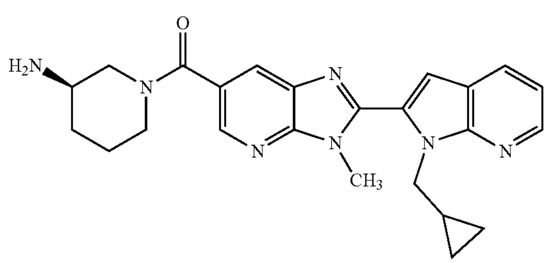 [SMILES: Cn1c(-c2cc3cccnc3n2CC2CC2)nc2cc(C(=O)N3CCC[C@@H](N)C3)cnc21] | I-7 | 429.518 | 1.74 min | 430 | A | HCl | 1 |
| 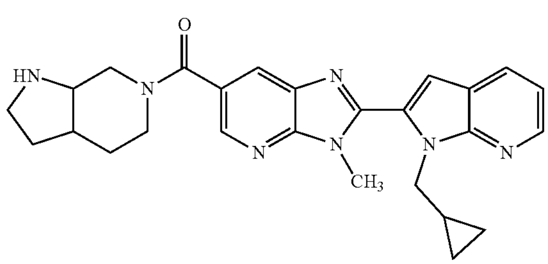 [SMILES: Cn1c(-c2cc3cccnc3n2CC2CC2)nc2cc(C(=O)N3CCC4CCNC4C3)cnc21] | I-8 | 455.555 | 1.79 min | 456 | A | HCl | 1 |
| 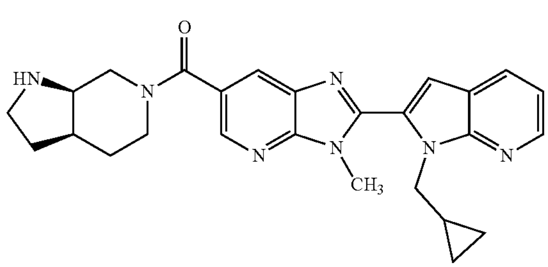 [SMILES: Cn1c(-c2cc3cccnc3n2CC2CC2)nc2cc(C(=O)N3CC[C@H]4CCN[C@H]4C3)cnc21] | I-9 | 455.555 | 1.77 min | 456 | A | HCl | 1 |

-continued

| Structure | # | Mol Wt | LCMS T$_{ret}$ | M/Z(+) | LCMS Method | Salt | Salt Stoichiometry |
|---|---|---|---|---|---|---|---|
| (structure) | I-10 | 455.555 | 1.79 min | 456 | A | HCl | 1 |
| (structure) | I-11 | 453.488 | 1.67 min | 454 | A | HCl | 1 |
| (structure) | I-12 | 479.525 | 1.97 min | 480 | A | HCl | 1 |
| (structure) | I-13 | 447.508 | 3.77 min | 448 | A | HCl | 1 |
| (structure) | I-14 | 464.510 | 2.32 min | 465 | A | HCl | 1 |
| (structure) | I-16 | 473.57 | 2.35 min | 474 | A | NA | NA |

-continued

| Structure | # | Mol Wt | LCMS T$_{ret}$ | M/Z(+) | LCMS Method | Salt | Salt Stoichiometry |
|---|---|---|---|---|---|---|---|
| 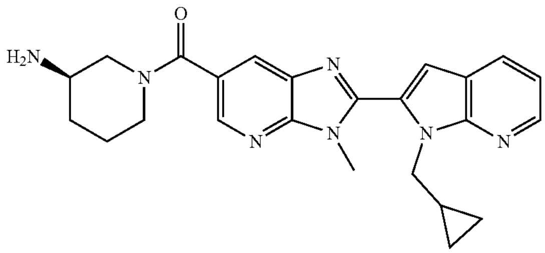 [SMILES: Cn1c(-c2cc3cccnc3n2CC2CC2)nc2cc(C(=O)N3CCC[C@@H](N)C3)cnc21] | I-17 | 429.52 | 1.74 min | 430.1 | A | HCl | 1 |
| 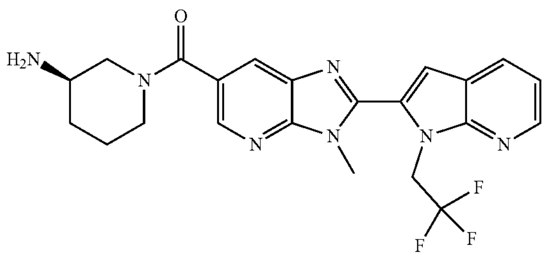 [SMILES: Cn1c(-c2cc3cccnc3n2CC(F)(F)F)nc2cc(C(=O)N3CCC[C@@H](N)C3)cnc21] | I-18 | 457.45 | 1.78 min | 458.1 | A | | |
| 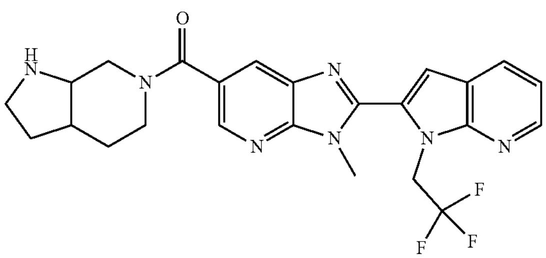 [SMILES: Cn1c(-c2cc3cccnc3n2CC(F)(F)F)nc2cc(C(=O)N3CCC4CCNC4C3)cnc21] | I-19 | 483.49 | 1.81 min | 484.1 | A | | |
| 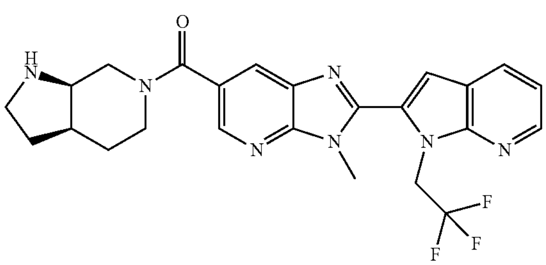 [SMILES: Cn1c(-c2cc3cccnc3n2CC(F)(F)F)nc2cc(C(=O)N3CC[C@H]4CCN[C@H]4C3)cnc21] | I-20 | 483.49 | 1.82 min | 484.1 | A | | |
| 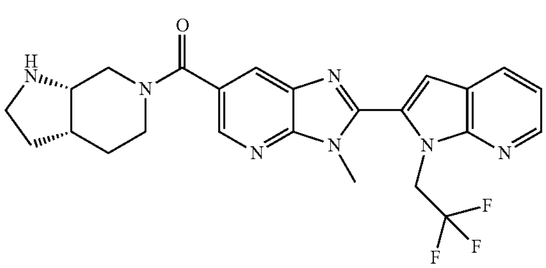 [SMILES: Cn1c(-c2cc3cccnc3n2CC(F)(F)F)nc2cc(C(=O)N3CC[C@@H]4CCN[C@@H]4C3)cnc21] | I-21 | 483.49 | 1.82 min | 484.1 | A | | |
| 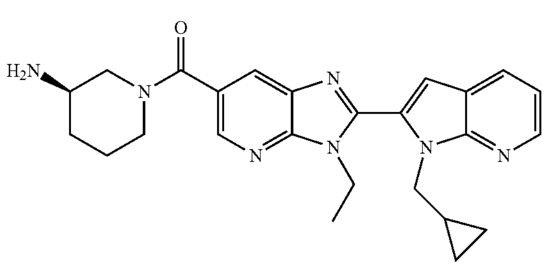 [SMILES: CCn1c(-c2cc3cccnc3n2CC2CC2)nc2cc(C(=O)N3CCC[C@@H](N)C3)cnc21] | I-22 | 443.54 | 1.88 min | 444.1 | A | HCl | 1 |

-continued

| Structure | # | Mol Wt | LCMS T$_{ret}$ | M/Z(+) | LCMS Method | Salt | Salt Stoichiometry |
|---|---|---|---|---|---|---|---|
| 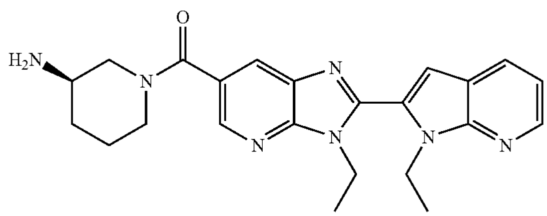 [SMILES: CCn1c(-c2nc3cc(C(=O)N4CCC[C@@H](N)C4)cnc3n2CC)cc2cccnc21] | I-23 | 417.51 | 1.68 min | 418.2 | A | HCl | 1 |
| 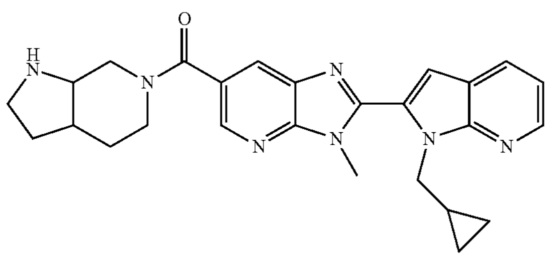 [SMILES: Cn1c(-c2cc3cccnc3n2CC2CC2)nc2cc(C(=O)N3CCC4CCNC4C3)cnc21] | I-24 | 455.55 | 1.79 min | 456.1 | A | HCl | 1 |
| 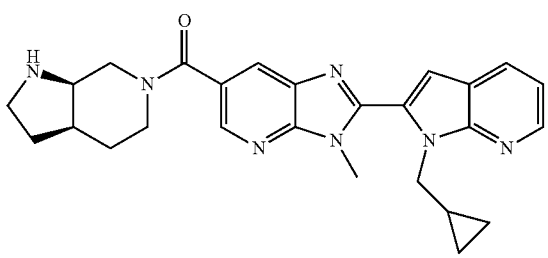 [SMILES: Cn1c(-c2cc3cccnc3n2CC2CC2)nc2cc(C(=O)N3CC[C@H]4CCN[C@H]4C3)cnc21] | I-25 | 455.55 | 1.77 min | 456.1 | A | HCl | 1 |
| 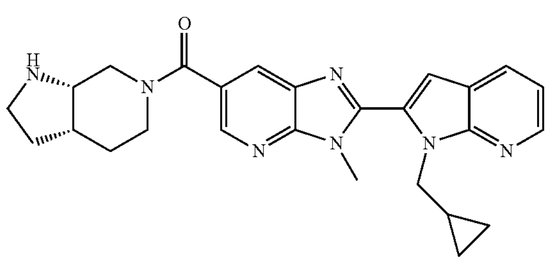 [SMILES: Cn1c(-c2cc3cccnc3n2CC2CC2)nc2cc(C(=O)N3CC[C@@H]4CCN[C@@H]4C3)cnc21] | I-26 | 455.55 | 1.79 min | 456.1 | A | HCl | 1 |
| 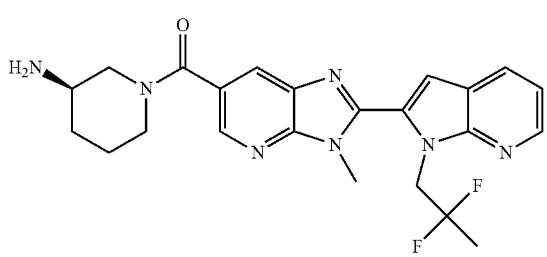 [SMILES: Cn1c(-c2cc3cccnc3n2CC(C)(F)F)nc2cc(C(=O)N3CCC[C@@H](N)C3)cnc21] | I-27 | 453.49 | 1.67 min | 454.2 | A | HCl | 1 |
| 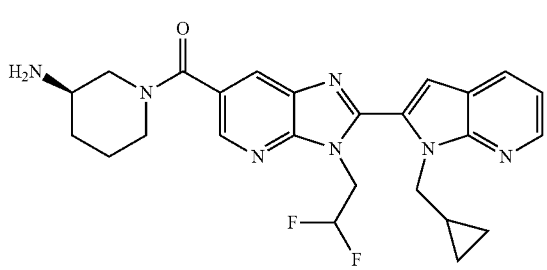 [SMILES: N[C@@H]1CCCN(C(=O)c2cnc3c(c2)nc(-c2cc4cccnc4n2CC2CC2)n3CC(F)F)C1] | I-28 | 479.53 | 1.97 min | 480.2 | A | HCl | 1 |

-continued
| Structure | # | Mol Wt | LCMS T$_{ret}$ | M/Z(+) | LCMS Method | Salt | Salt Stoichiometry |
|---|---|---|---|---|---|---|---|
| 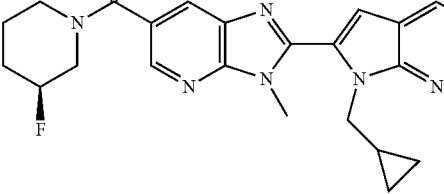 | I-29 | 447.51 | 3.77 min | 448.3 | B | HCl | 1 |
| 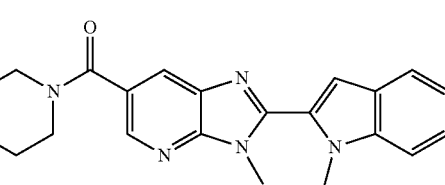 | I-30 | 464.51 | 2.32 min | 465.2 | A | HCl | 1 |
| 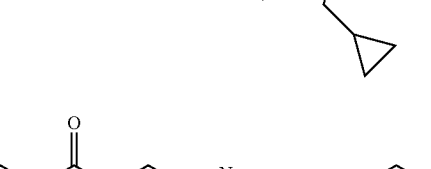 | I-31 | 473.57 | 2.35 min | 474.3 | A | | |
| 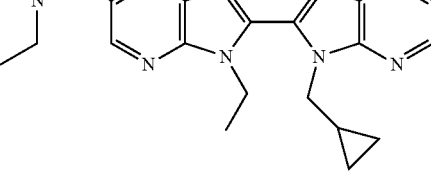 | I-32 | 443.54 | 1.86/ 1.88 min | 444.2/ 444.3 | A | HCl | 1 |
| 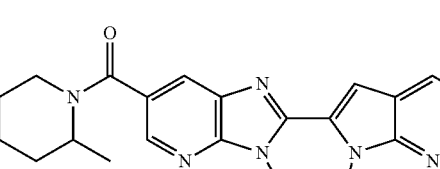 | I-33 | 415.49 | 1.55 min | 416.3 | A | HCl | 1 |
| 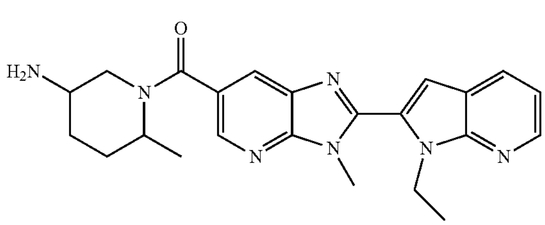 [SMILES: CCn1c(-c2nc3cc(C(=O)N4CC(N)CCC4C)cnc3n2C)cc2cccnc21] | I-34 | 417.51 | 1.67 min | 418.3 | A | HCl | 1 |

| Structure | # | Mol Wt | LCMS T$_{ret}$ | M/Z(+) | LCMS Method | Salt | Salt Stoichiometry |
|---|---|---|---|---|---|---|---|
| 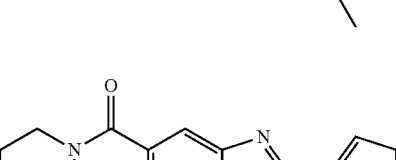 | I-35 | 417.51 | 1.64 min | 418.2 | A | HCl | 1 |
| 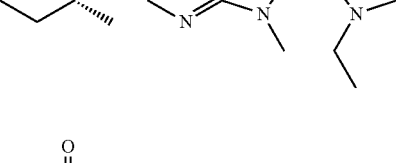 | I-36 | 417.51 | 1.65 min | 418.2 | A | HCl | 1 |
| 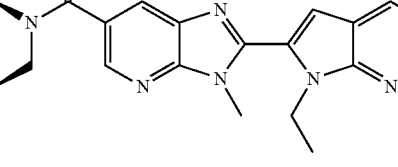 | I-37 | 445.52 | 2.08 min | 446.2 | A | HCl | 1 |
| 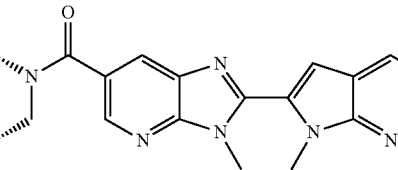 | I-38 | 445.52 | 2.07 min | 446.2 | A | HCl | 1 |
| 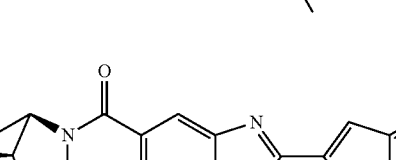 | I-39 | 415.49 | 1.55 min | 416.2 | A | HCl | 2 |
| 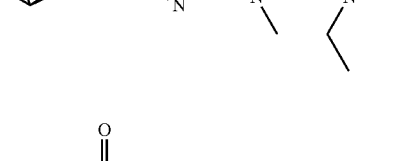 | I-40 | 415.49 | 1.54 min | 416.2 | A | HCl | 2 |

-continued

| Structure | # | Mol Wt | LCMS T$_{ret}$ | M/Z(+) | LCMS Method | Salt | Salt Stoichiometry |
|---|---|---|---|---|---|---|---|
| 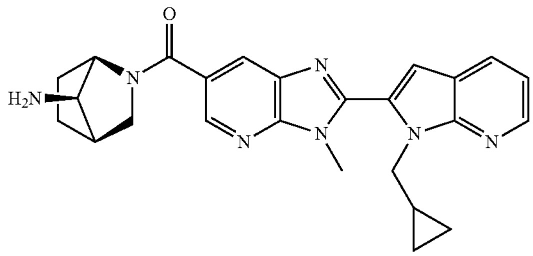 [SMILES: Cn1c(-c2cc3cccnc3n2CC2CC2)nc2cc(C(=O)N3C[C@H]4CC[C@@H]3[C@@H]4N)cnc21] | I-41 | 441.53 | 1.76 min | 442.3 | A | HCl | 2 |
| 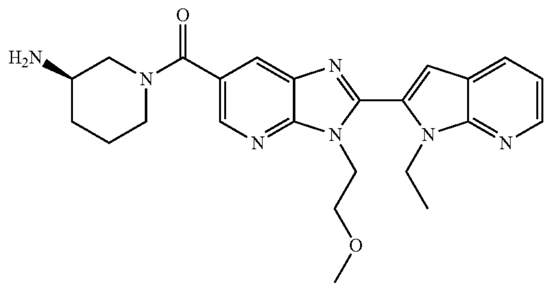 [SMILES: CCn1c(-c2nc3cc(C(=O)N4CCC[C@@H](N)C4)cnc3n2CCOC)cc2cccnc21] | I-42 | 447.53 | 1.64 min | 448.2 | A | HCl | 1 |
| 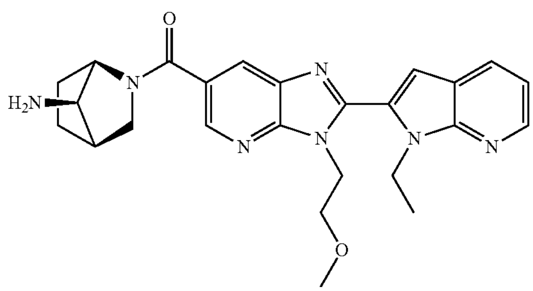 [SMILES: CCn1c(-c2nc3cc(C(=O)N4C[C@H]5CC[C@@H]4[C@@H]5N)cnc3n2CCOC)cc2cccnc21] | I-43 | 459.54 | 1.62 min | 460.2 | A | HCl | 1 |
| 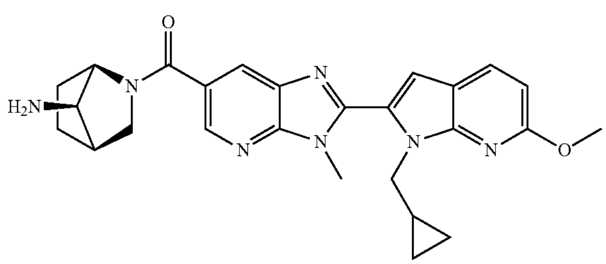 [SMILES: COc1ccc2cc(-c3nc4cc(C(=O)N5C[C@H]6CC[C@@H]5[C@@H]6N)cnc4n3C)n(CC3CC3)c2n1] | I-44 | 471.55 | 2.24 min | 472.1 | A | | |
| 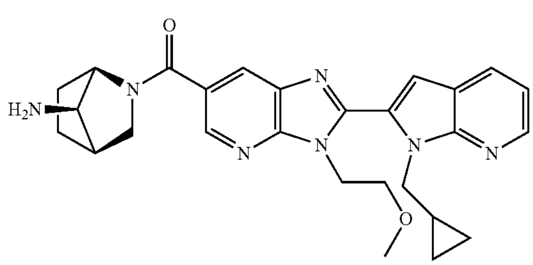 [SMILES: COCCn1c(-c2cc3cccnc3n2CC2CC2)nc2cc(C(=O)N3C[C@H]4CC[C@@H]3[C@@H]4N)cnc21] | I-45 | 485.58 | 1.87 min | 486.2 | A | HCl | 1 |

-continued

| Structure | # | Mol Wt | LCMS T$_{ret}$ | M/Z(+) | LCMS Method | Salt | Salt Stoichiometry |
|---|---|---|---|---|---|---|---|
| 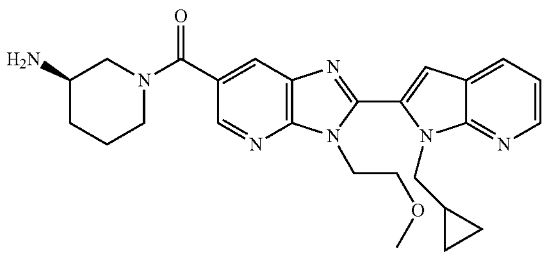 [SMILES: COCCn1c(-c2cc3cccnc3n2CC2CC2)nc2cc(C(=O)N3CCC[C@@H](N)C3)cnc21] | I-46 | 473.57 | 1.89 min | 474.2 | A | HCl | 1 |
| 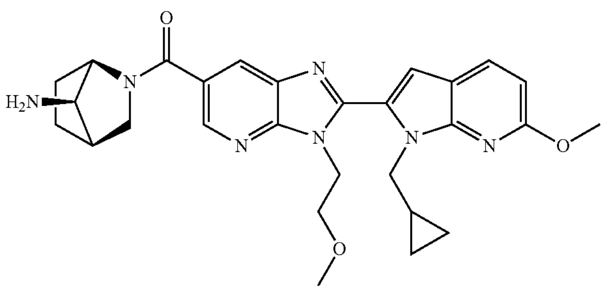 [SMILES: COCCn1c(-c2cc3ccc(OC)nc3n2CC2CC2)nc2cc(C(=O)N3C[C@H]4CC[C@@H]3[C@@H]4N)cnc21] | I-47 | 515.61 | 2.33 min | 516.2 | A | | |
| 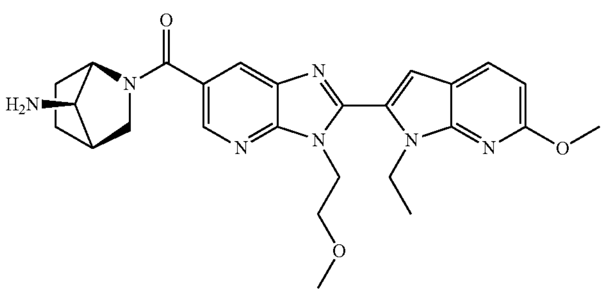 [SMILES: CCn1c(-c2nc3cc(C(=O)N4C[C@H]5CC[C@@H]4[C@@H]5N)cnc3n2CCOC)cc2ccc(OC)nc21] | I-48 | 489.57 | 2.14 min | 490.2 | A | HCl | 1 |
| 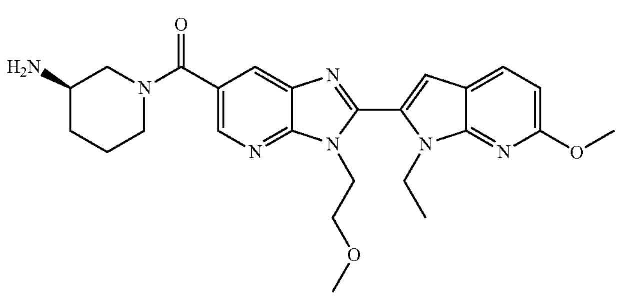 [SMILES: CCn1c(-c2nc3cc(C(=O)N4CCC[C@@H](N)C4)cnc3n2CCOC)cc2ccc(OC)nc21] | I-49 | 477.56 | 2.14 min | 478.2 | A | HCl | 1 |
| 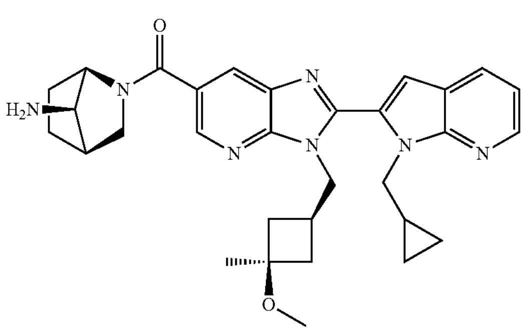 [SMILES: CO[C@]1(C)C[C@H](Cn2c(-c3cc4cccnc4n3CC3CC3)nc3cc(C(=O)N4C[C@H]5CC[C@@H]4[C@@H]5N)cnc32)C1] | I-50 | 539.67 | 2.12 min | 540.4 | A | HCl | 1 |

-continued

| Structure | # | Mol Wt | LCMS T$_{ret}$ | M/Z(+) | LCMS Method | Salt | Salt Stoichiometry |
|---|---|---|---|---|---|---|---|
| 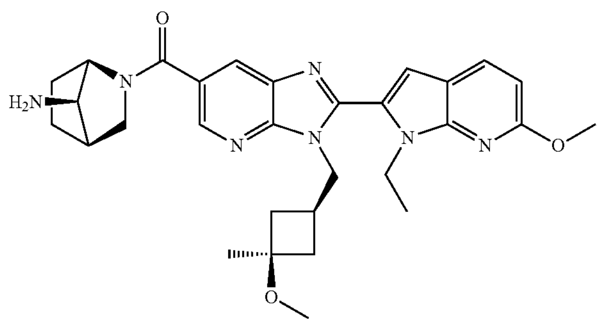 [SMILES: CCn1c(-c2nc3cc(C(=O)N4C[C@H]5CC[C@@H]4[C@@H]5N)cnc3n2C[C@H]2C[C@@](C)(OC)C2)cc2ccc(OC)nc21] | I-51 | 543.66 | 2.37 min | 544.5 | A | HCl | 1 |
| 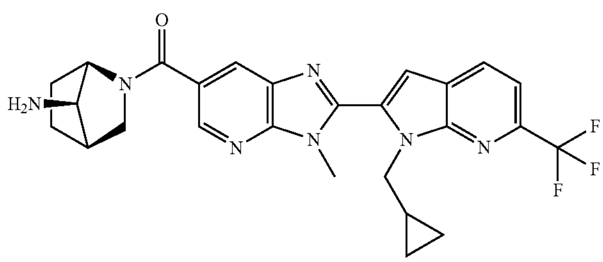 [SMILES: Cn1c(-c2cc3ccc(C(F)(F)F)nc3n2CC2CC2)nc2cc(C(=O)N3C[C@H]4CC[C@@H]3[C@@H]4N)cnc21] | I-52 | 509.53 | 2.45 min | 510.3 | A | HCl | 1 |
| 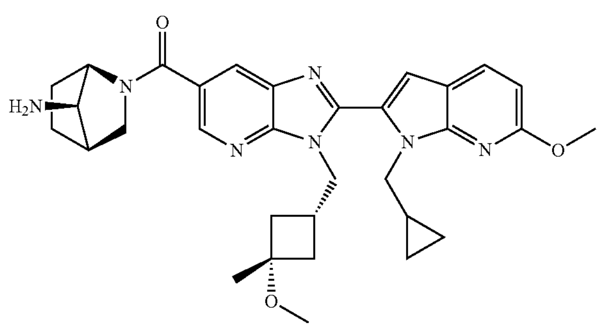 [SMILES: COc1ccc2cc(-c3nc4cc(C(=O)N5C[C@H]6CC[C@@H]5[C@@H]6N)cnc4n3C[C@H]3C[C@@](C)(OC)C3)n(CC3CC3)c2n1] | I-53 | 569.7 | 2.57 min | 570.3 | A | HCl | 1 |
| 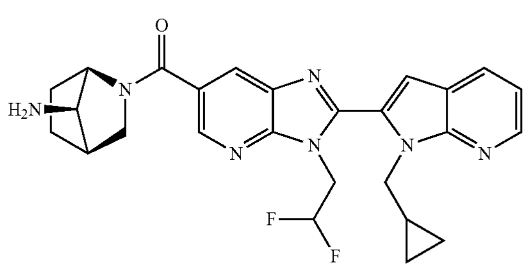 [SMILES: N[C@@H]1[C@@H]2CC[C@H]1N(C(=O)c1cnc3c(c1)nc(-c1cc4cccnc4n1CC1CC1)n3CC(F)F)C2] | I-54 | 491.54 | 1.97 min | 492.2 | A | HCl | 1 |
| 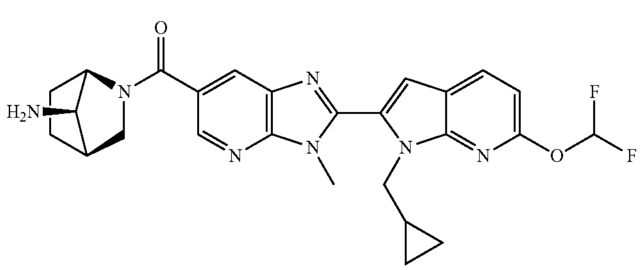 [SMILES: Cn1c(-c2cc3ccc(OC(F)F)nc3n2CC2CC2)nc2cc(C(=O)N3C[C@H]4CC[C@@H]3[C@@H]4N)cnc21] | I-55 | 507.54 | 2.36 min | 508.2 | A | HCl | 1 |

-continued
| Structure | # | Mol Wt | LCMS T$_{ret}$ | M/Z(+) | LCMS Method | Salt | Salt Stoichiometry |
|---|---|---|---|---|---|---|---|
| 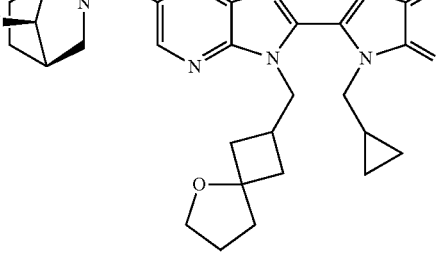 | I-56 | 551.68 | 2.08 min | 552.3 | A | | |
| 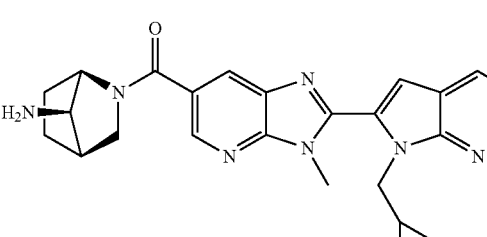 | I-57 | 499.61 | 3.62 min | 500.3 | H | HCl | 1 |
| 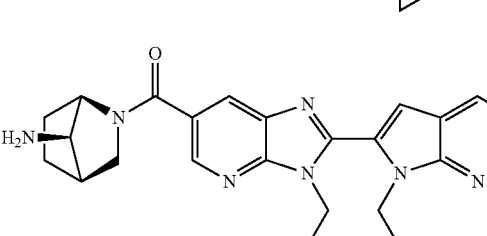 | I-58 | 555.67 | 2.35 min | 556.4 | A | | |
| 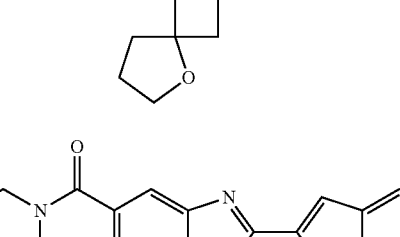 | I-59 | 543.66 | 2.39 min | 544.4 | A | | |
| 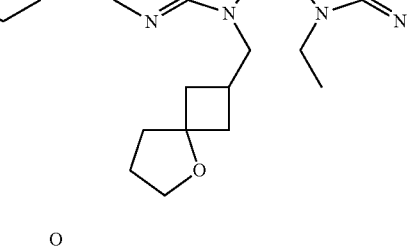 | I-60 | 495.52 | 2.31 min | 496.3 | A | HCl | 1 |

-continued

| Structure | # | Mol Wt | LCMS T$_{ret}$ | M/Z(+) | LCMS Method | Salt | Salt Stoichiometry |
|---|---|---|---|---|---|---|---|
| 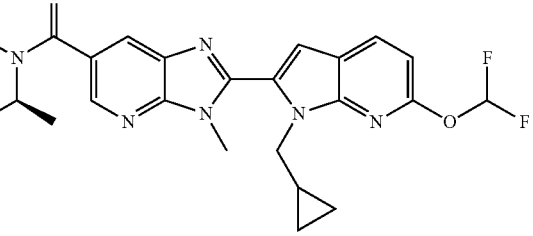 | I-61 | 509.55 | 2.41 min | 510.3 | A | | |
| 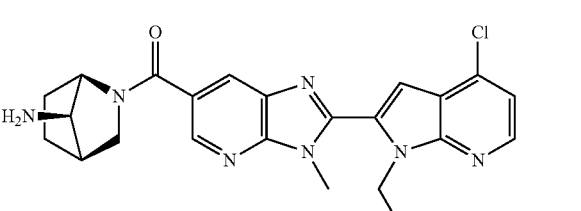 | I-62 | 475.97 | 2.06 min | 476.3 | A | HCl | 1 |
| 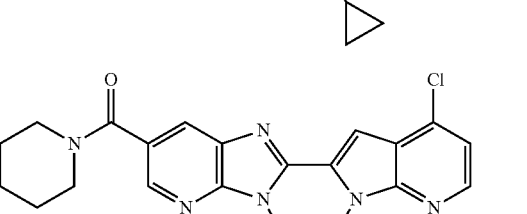 | I-63 | 463.96 | 2.09 min | 464.3 | A | HCl | 1 |
| 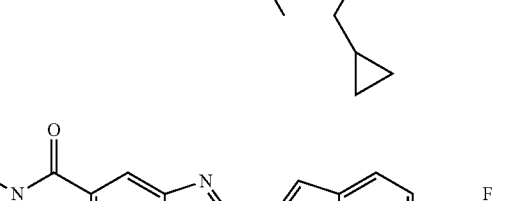 | I-64 | 513.51 | 2.35 min | 514.3 | A | Hydrochloric acid | 1 |

Biological Assays

Compounds of the present invention were assayed as inhibitors of PAD4 using the assay protocol described below.

Compounds were solubilised in 100% DMSO to achieve 100 mM final compound concentration. Compound stock solutions were stored at RT. A series of dilutions were prepared in DMSO and mixed 8 times with 20 µL mixing volume. Final assay conditions were as follows:
Reaction volume: 20 µl
Assay buffer (as aforementioned): 100 mM Tris-HCl (pH 7.6), 2 mM DTT, 1 mM CaCl$_2$
Final concentrations:
100 nM hPAD4 enzyme
50 µM (8-fold sub-K$_m$) substrate peptide
0.5% DMSO
Total incubation time: 65 mins at 37° C.
Stop solution: 40 µl 5% TCA in ACN
0.25 µL of compound solution was added to 10 µL of 200 nM PAD4 in assay buffer (100 mM Tris-HCl pH 7.6, 2 mM DTT). After 5 mins, 10 µL of 100 µM of substrate in buffer (100 mM Tris-HCl pH 7.6, 2 mM DTT, 2 mM CaCl2) was added and the reaction incubated for 60 mins at 37° C. The enzymatic reaction was quenched by addition of 40 µl of 5% TCA in ACN (1.7% TCA final concentration) stop solution. Arginine containing substrate and citrulline containing product (+1 Da mass shift) were subjected to solid phase extraction on Agilent RapidFire (RF) 300 system and detected on a coupled, triple quadrupole Agilent 6460 QQQ mass spectrometry (MS) device under application of multiple reaction monitoring (MRM) for quantitation.

Table 2, below, shows the activity of selected compounds of this invention in the PAD4 assays described above. The compound numbers correspond to the compound numbers in Table 1. Compounds having an activity designated as "A" provided an IC$_{50}$≤1 µM; compounds having an activity designated as "B" provided an IC$_{50}$ of 1.0-5.0 µM; compounds having an activity designated as "C" provided an IC$_{50}$ of 5.0-10.0 µM; and compounds having an activity designated as "D" provided an IC$_{50}$ of ≥10.0 μM. The term pIC$_{50}$=−log(IC$_{50}$). Compounds having an activity designated as "E" provided a pIC$_{50}$≤4; compounds having an activity designated as "F" provided a pIC$_{50}$ of 4.0-5.0; compounds having an activity designated as "G" provided a pIC$_{50}$ of 5.0-6.0; and compounds having an activity designated as "H" provided a pIC$_{50}$ of ≥6. "NA" stands for "not assayed."

TABLE 2

PAD4 Activity

| Compound # | hPAD4 RFMS IC50 uM | hPAD4 RFMS pIC50 | mPAD4 RFMS IC50 uM | mPAD4 RFMS pIC50 |
|---|---|---|---|---|
| I-1 | D | F | NA | NA |
| I-2 | B | G | A | H |
| I-3 | D | F | NA | NA |
| I-4 | C | G | B | G |
| I-5 | D | F | NA | NA |
| I-6 | D | F | NA | NA |
| I-7 | B | G | A | H |
| I-8 | C | G | NA | NA |
| I-9 | D | F | NA | NA |
| I-10 | B | G | C | G |
| I-11 | C | G | C | G |
| I-12 | B | G | B | G |
| I-13 | B | G | A | H |
| I-14 | B | G | A | H |
| I-16 | A | H | A | H |
| I-17 | B | G | A | H |
| I-18 | D | F | NA | NA |
| I-19 | D | F | NA | NA |
| I-20 | D | F | NA | NA |
| I-21 | D | E/F | NA | NA |
| I-22 | B | G | A | H |
| I-23 | C | G | B | G |
| I-24 | C | G | NA | NA |
| I-25 | D | F | NA | NA |
| I-26 | B | G | C | G |
| I-27 | C | G | C | G |
| I-28 | B | G | B | G |
| I-29 | B | G | A | H |
| I-30 | B | G | A | H |
| I-31 | A | H | A | H |
| I-32 | B | G | C | G |
| I-37 | A | H | A | H |
| I-39 | B | G | B | G |
| I-41 | A | H | A | H |
| I-42 | D | F | B | G |
| I-43 | B | G | B | G |
| I-44 | A | H | A | H |
| I-45 | A | H | B | G |
| I-46 | B | G | B | G |
| I-47 | A | H | A | H |
| I-48 | A | H | B | G |
| I-49 | C | G | B | G |
| I-50 | A | H | A | H |
| I-51 | A | H | A | H |
| I-52 | A | H | A | H |
| I-53 | A | H | A | H |
| I-54 | A | H | A | H |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I':

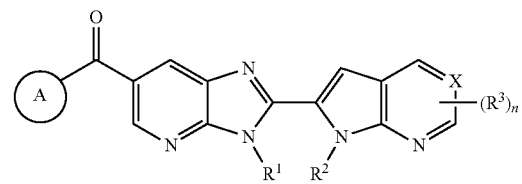

or a pharmaceutically acceptable salt thereof, wherein:

R$^1$ is hydrogen, —CN, —OR,

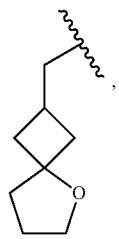 [SMILES: *CC1CC2(CCCO2)C1]

or C$_{1-6}$ aliphatic optionally substituted with 1-4 groups selected from fluorine, —CN, or OR;

R$^2$ is hydrogen or C$_{1-10}$ aliphatic optionally substituted with 1-5 groups selected from fluorine, —CN, or —OR;

Ring A is

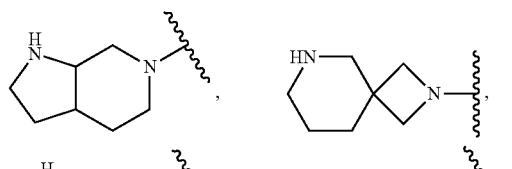

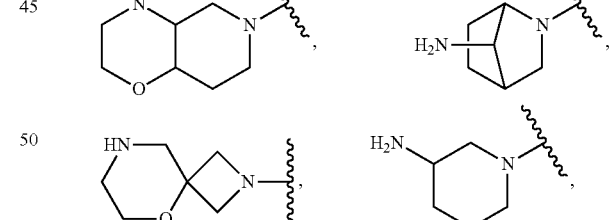

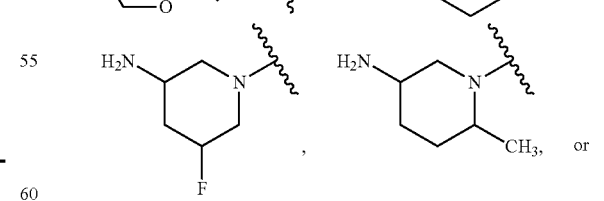

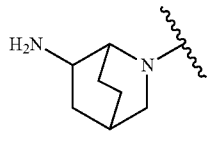

wherein Ring A is optionally substituted with 1-4 groups selected from fluorine, —CN, —OR, or C$_{1-6}$ aliphatic optionally substituted with 1-3 fluorine atoms;
each R³ is independently halogen, —CN, —R, or —OR;
X is C or N;
n is 0-3; and
each R is independently hydrogen or C$_{1-6}$ aliphatic optionally substituted with —OH or with 1-3 fluorine atoms.

2. The compound according to claim 1, wherein Ring A is

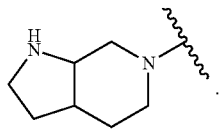 [SMILES: *N1CCC2CCNC2C1]

3. The compound according to claim 2, wherein Ring A is

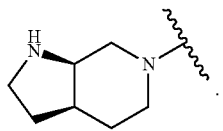 [SMILES: *N1CC[C@H]2CCN[C@H]2C1]

4. The compound according to claim 2, wherein Ring A is

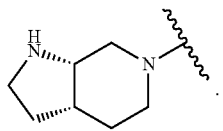 [SMILES: *N1CC[C@@H]2CCN[C@@H]2C1]

5. The compound according to claim 1, wherein Ring A is

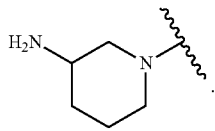

6. The compound according to claim 5, wherein Ring A is

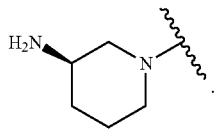

7. The compound according to claim 5, wherein Ring A is

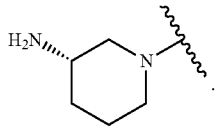

8. The compound according to claim 1, wherein Ring A is

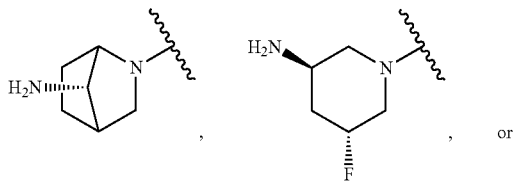

, or

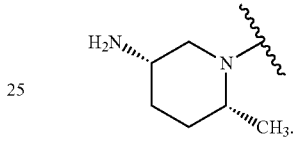

9. The compound according to claim 1, wherein Ring A is

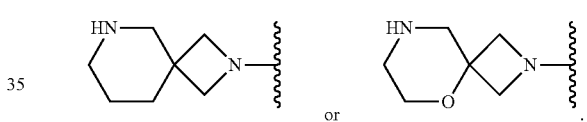

10. The compound according to claim 1, wherein R¹ is C$_{1-3}$ aliphatic optionally substituted with 1, 2, or 3 fluorine atoms.

11. The compound according to claim 10, wherein R¹ is methyl, ethyl, or propyl.

12. The compound according to claim 10, wherein R¹ is methyl, ethyl, or propyl, wherein each methyl, ethyl, or propyl is substituted with 1, 2, or 3 fluorine atoms.

13. The compound according to claim 12, wherein R² is C$_{1-10}$ aliphatic optionally substituted with 1-5 fluorine atoms.

14. The compound according to claim 13, wherein R² is cyclopropylmethyl, trifluoroethyl, or difluoropropyl.

15. A pharmaceutically acceptable composition comprising the compound according to claim 1, and a pharmaceutically acceptable carrier, adjuvant, or vehicle.

16. The composition according to claim 15, in combination with an additional therapeutic agent.

17. A method of inhibiting PAD4 in a subject or in a biological sample comprising the step of contacting the PAD4 with a compound according to claim 1.

* * * * *